US012006537B2

(12) United States Patent
Do et al.

(10) Patent No.: US 12,006,537 B2
(45) Date of Patent: *Jun. 11, 2024

(54) DIGITAL ASSAYS WITH A GENERIC REPORTER

(71) Applicant: Bio-Rad Laboratories, Inc., Hercules, CA (US)

(72) Inventors: Duc Do, San Jose, CA (US); Claudia Litterst, Walnut Creek, CA (US); Dianna Maar, Mountain House, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/855,199

(22) Filed: Jun. 30, 2022

(65) Prior Publication Data

US 2023/0057343 A1 Feb. 23, 2023

Related U.S. Application Data

(60) Continuation of application No. 15/973,243, filed on May 7, 2018, now Pat. No. 11,377,684, which is a division of application No. 14/191,295, filed on Feb. 26, 2014, now Pat. No. 9,970,052, which is a continuation-in-part of application No. 13/973,940, filed on Aug. 22, 2013, now Pat. No. 9,702,822.

(60) Provisional application No. 61/864,792, filed on Aug. 12, 2013, provisional application No. 61/789,703, filed on Mar. 15, 2013, provisional application No. 61/692,635, filed on Aug. 23, 2012.

(51) Int. Cl.
*C12Q 1/68* (2018.01)
*C12Q 1/6844* (2018.01)
*C12Q 1/686* (2018.01)
*G01N 21/64* (2006.01)

(52) U.S. Cl.
CPC .......... *C12Q 1/686* (2013.01); *C12Q 1/6844* (2013.01); *G01N 21/6408* (2013.01)

(58) Field of Classification Search
None
See application file for complete search history.

(56) References Cited

U.S. PATENT DOCUMENTS

| | | | |
|---|---|---|---|
| 5,304,810 A | 4/1994 | Amos | |
| 6,020,141 A | 2/2000 | Pantoliano et al. | |
| 7,801,226 B2 | 9/2010 | Suh et al. | |
| 8,148,515 B1 | 4/2012 | Mao et al. | |
| 8,951,939 B2 | 2/2015 | Saxonov et al. | |
| 9,156,010 B2 | 10/2015 | Colston, Jr. et al. | |
| 9,217,175 B2 | 12/2015 | Regan et al. | |
| 9,222,128 B2 | 12/2015 | Saxonv et al. | |
| 9,458,511 B2 | 10/2016 | Koehler et al. | |
| 9,523,116 B2 | 12/2016 | Tzonev et al. | |
| 9,702,822 B2 | 7/2017 | Litterst et al. | |
| 2005/0266448 A1 | 12/2005 | Hagiwara et al. | |
| 2006/0078888 A1 | 4/2006 | Griffiths et al. | |
| 2009/0069194 A1 | 3/2009 | Ramakrishnan | |
| 2009/0239308 A1 | 9/2009 | Dube et al. | |
| 2009/0311713 A1 | 12/2009 | Pollack et al. | |
| 2010/0022414 A1 | 1/2010 | Link et al. | |
| 2010/0092973 A1 | 4/2010 | Davies et al. | |
| 2010/0173394 A1* | 7/2010 | Colston, Jr. | B01L 3/502715 422/68.1 |
| 2010/0233686 A1 | 9/2010 | Higuchi et al. | |
| 2010/0248385 A1 | 9/2010 | Tan et al. | |
| 2010/0304978 A1 | 12/2010 | Deng et al. | |
| 2011/0000560 A1 | 1/2011 | Miller et al. | |
| 2011/0104686 A1 | 5/2011 | Litterst et al. | |
| 2011/0159499 A1 | 6/2011 | Hindson et al. | |
| 2011/0244455 A1 | 10/2011 | Larson et al. | |
| 2011/0250597 A1 | 10/2011 | Larson et al. | |
| 2012/0122714 A1 | 5/2012 | Samuels et al. | |
| 2012/0164690 A1 | 6/2012 | Wang | |
| 2012/0208241 A1 | 8/2012 | Link | |
| 2012/0219947 A1 | 8/2012 | Yurkovetsky et al. | |
| 2012/0220494 A1 | 8/2012 | Samuels et al. | |
| 2012/0252015 A1 | 10/2012 | Hindson et al. | |
| 2012/0264646 A1 | 10/2012 | Link et al. | |
| 2012/0302448 A1 | 11/2012 | Hutchison et al. | |
| 2012/0309002 A1 | 12/2012 | Link | |
| 2012/0316074 A1 | 12/2012 | Saxonov | |
| 2012/0322058 A1 | 12/2012 | Regan et al. | |
| 2012/0329664 A1 | 12/2012 | Saxonov et al. | |
| 2013/0017968 A1 | 1/2013 | Gurtner et al. | |

(Continued)

FOREIGN PATENT DOCUMENTS

AU 2012129187 A1 9/2012
WO 03064691 A2 8/2003

(Continued)

OTHER PUBLICATIONS

Nakano, M. et al. Single molecule PCR using water-in-oil-emulsions. Journal of Biotechnology, vol. 102, p. 117-124, 2003.*
Arya, Manit et al., "Basic principles of real-time quantitative PCR", Expert Review of Molecular Diagnostics, vol. 5, No. 2, (2005), 11 pages.
Zhong, Qun, "Multiplex digital PCR: breaking the one target per color barrier of quantitative PCR", Lab Chip, vol. 11, (2011), pp. 2167-2174.
European Patent Office, "Communication Pursuant to Article 94(3) EPC", in connection with related European Patent Application No. 14769970.6, dated Mar. 31, 2017, 3 pages.

(Continued)

*Primary Examiner* — Suryaprabha Chunduru
(74) *Attorney, Agent, or Firm* — Withers Bergman LLP; Thomas C. Meyers

(57) ABSTRACT

Digital assay system, including methods, apparatus, and compositions, for assay of one or more targets in a set of partitions containing a generic reporter of target amplification.

15 Claims, 17 Drawing Sheets

(56) References Cited

U.S. PATENT DOCUMENTS

| | | | |
|---|---|---|---|
| 2013/0040841 A1* | 2/2013 | Saxonov | C12Q 1/6851 506/9 |
| 2013/0059754 A1 | 3/2013 | Tzonev | |
| 2013/0178378 A1 | 7/2013 | Hatch et al. | |
| 2014/0057273 A1 | 2/2014 | Litterst et al. | |
| 2014/0171341 A1 | 6/2014 | Jouvenot et al. | |
| 2014/0221237 A1 | 8/2014 | Tzonev et al. | |
| 2014/0221238 A1 | 8/2014 | Regan et al. | |

FOREIGN PATENT DOCUMENTS

| | | | |
|---|---|---|---|
| WO | 2006002167 A2 | 1/2006 | |
| WO | 2010018465 A2 | 2/2010 | |
| WO | 2010036352 A1 | 4/2010 | |
| WO | 2011100604 A2 | 8/2011 | |
| WO | 2011143478 A2 | 11/2011 | |
| WO | WO-2011142836 A2 * | 11/2011 | C12Q 1/6851 |
| WO | 2012129187 A1 | 9/2012 | |
| WO | 2014031908 A1 | 2/2014 | |
| WO | 2014121239 A2 | 8/2014 | |
| WO | 2014121240 A1 | 8/2014 | |

OTHER PUBLICATIONS

Beer, N. Reginald et al., "On-Chip, Real-Time, Single-Copy Polymerase Chain Reaction in Picoliter Droplets", Analytical Chemistry, vol. 79, No. 22, Nov. 15, 2007, pp. 8471-8475.

Bhagwat, Arvind A., "Simultaneous detection of *Escherichia coli* O157:H7, Listeria monocytogenes and *Salmonella* strains by real-time PCR", International Journal of Food Microbiology, vol. 84, (2003), pp. 217-224.

Blaine R. Copenheaver, Authorized Officer, International Searching Authority, U.S. Patent and Trademark Office, "International Searching Report" in connection with related PCT Patent Application No. PCT/US2014/018785, dated May 15, 2014, 3 pages.

Blaine R. Copenheaver, Authorized Officer, International Searching Authority, U.S. Patent and Trademark Office, "Written Opinion of the International Searching Authority" in connection with related PCT Patent Application No. PCT/US2014/018785, dated May 15, 2014, 12 pages.

Butler, John M., "Capillary electrophoresis as a tool for optimization of multiplex PCR reactions", Fresenius J Analytical Chemistry, vol. 369, (2001), pp. 200-205.

Cawthon, Richard M., "Telomere measurement by quantitative PCR", Nucleic Acids Research, vol. 30, No. 10, (2002), pp. 1-6.

Dube, Simant et al., "Mathematical Analysis of Copy Number Variation in a DNA Sample Using Digital PCR on a Nanofluidic Device", PLoS ONE, vol. 3, Issue 8, Aug. 2008, pp. 1-9.

Zimmermann, Bernhard G. et al., "Digital PCR: a powerful new tool for noninvasive prenatal diagnosis?", Prenatal Diagnosis, vol. 28, Nov. 10, 2008, pp. 1087-1093.

Higuchi, Russell et al., "Simultaneous Amplification and Detection of Specific DNA Sequences", Biotechnology, vol. 10, Apr. 1992, pp. 413-417.

Higuchi, Russell et al., "Kinetic PCR Analysis: Real-time Monitoring of DNA Amplification Reactions", Biotechnology, vol. 11, Sep. 11, 1993, pp. 1026-1030.

Hindson, Benjamin J. et al., "High-Throughput Droplet Digital PCR System for Absolute Quantitation of DNA Copy Number", Analytical Chemistry, vol. 83, Oct. 28, 2011, pp. 8604-8610.

Hua, Zhishan et al., "Multiplexed Real-Time Polymerase Chain Reaction on a Digital Microfluidic Platform" Analytical Chemistry, vol. 82, No. 6, Mar. 15, 2010, pp. 2310-2316.

Kiss, Margaret Macris et al., "High-Throughput Quantitative Polymerase Chain Reaction in Picoliter Droplets", Analytical Chemistry, vol. 80, No. 23, Dec. 1, 2008, pp. 8975-8981.

Lind, Kristina et al., "Combining sequence-specific probes and DNA binding dyes in real-time PCR for specific nucleic acid quantification and melting curve analysis", Biotechniques, vol. 40, No. 3, Mar. 2006, pp. 315-319.

Mao, Fei et al., "Characterization of EvaGreen and the implication of its physicochemical properties for qPCR applications", BMC Technology, vol. 7, No. 76, Nov. 9, 2007, pp. 1-16.

Markey, Amelia L. et al., "High-throughput droplet PCR", Methods, vol. 50, Feb. 2, 2010, pp. 277-281.

Martin, Kendall J. et al., "Fungal-specific PCR primers developed for analysis of the ITS region of environmental DNA extracts", BMC Microbiology, vol. 5, No. 28, May 18, 2005, pp. 1-11.

McDermott, Geoffrey p et al., "Multiplexed Target Detection Using DNA-Binding Dye Chemistry in Droplet Digital PCR", Analytical Chemistry, vol. 85, Nov. 3, 2013, pp. 11619-11627.

Ottesen, Elizabeth A. et al., "Microfluidic Digital PCR Enables Multigene Analysis of Individual Environmental Bacteria", Science, vol. 314, Dec. 1, 2006, pp. 1464-1467.

Pekin, Deniz, "Quantitative and Sensitive Detection of Rare Mutations Using Droplet-Based Microfluidics", Lab Chip, vol. 11, (2011), pp. 2156-2166.

Pinheiro, Leonardo B. et al., "Evaluation of a Droplet Digital Polymerase Chain Reaction Format for DNA Copy Number Quantification", Analytical Chemistry, vol. 84, Nov. 28, 2011, pp. 1003-1011.

Pohl, Gudrun et al., "Principle and applications of digital PCR", Expert Review of Molecular Diagnostics, vol. 4, No. 1 (2004) pp. 41-47.

Qin, Jian et al., "Studying copy number variations using a nanofluidic platform", Nucleic Acids Research, vol. 36, No. 18, Aug. 18, 2008, pp. 1-8.

Schaerli, Yolanda et al., "The potential of microfluidic water-in-oil droplets in experimental biology", Molecular BioSystems, vol. 5, Oct. 12, 2009, pp. 1392-1404.

Therianos, Stavros et al., "Single-Channel Quantitative Multiplex Reverse Transcriptase-Polymerase Chain Reaction for Large Numbers for Gene Products Differentiates Nondemented from Neuropathological Alzheimer's Disease", American Journal of Pathology, vol. 164, No. 3, Mar. 2004, pp. 795-806.

Todorov, Tihomir et al,. "A Unified Rapid PCR Method for Detection of Normal and Expanded Trinucleotide Alleles of CAG Repeats in Huntington Chorea and CGG Repeats and Fragile X Syndrome", Molecular Biotechnology, Vo. 45, Mar. 9, 2010, pp. 150-154.

Vogelstein, Bert et al., "Digital PCR", Proceedings of the National Academy of Science USA, vol. 96, Aug. 1999, Genetics, pp. 9236-9241.

Wang, Weijie et al., "DNA quantification using EvaGreen and a real-time PCR instrument", Analytical Biochemistry, vol. 356, Jun. 9, 2006, pp. 303-305.

Wu, Yajun et al., "Detection of olive oil using the Evagreen real-time PCR method", European Food Research and Technology, vol. 227, Feb. 13, 2008, pp. 1117-1124.

Ye, Shu et al., "An efficient procedure for genotyping single nucleotide polymorphisms", Nucleic Acids Research, vol. 29, No. 17, (2001), pp. 1-8.

* cited by examiner

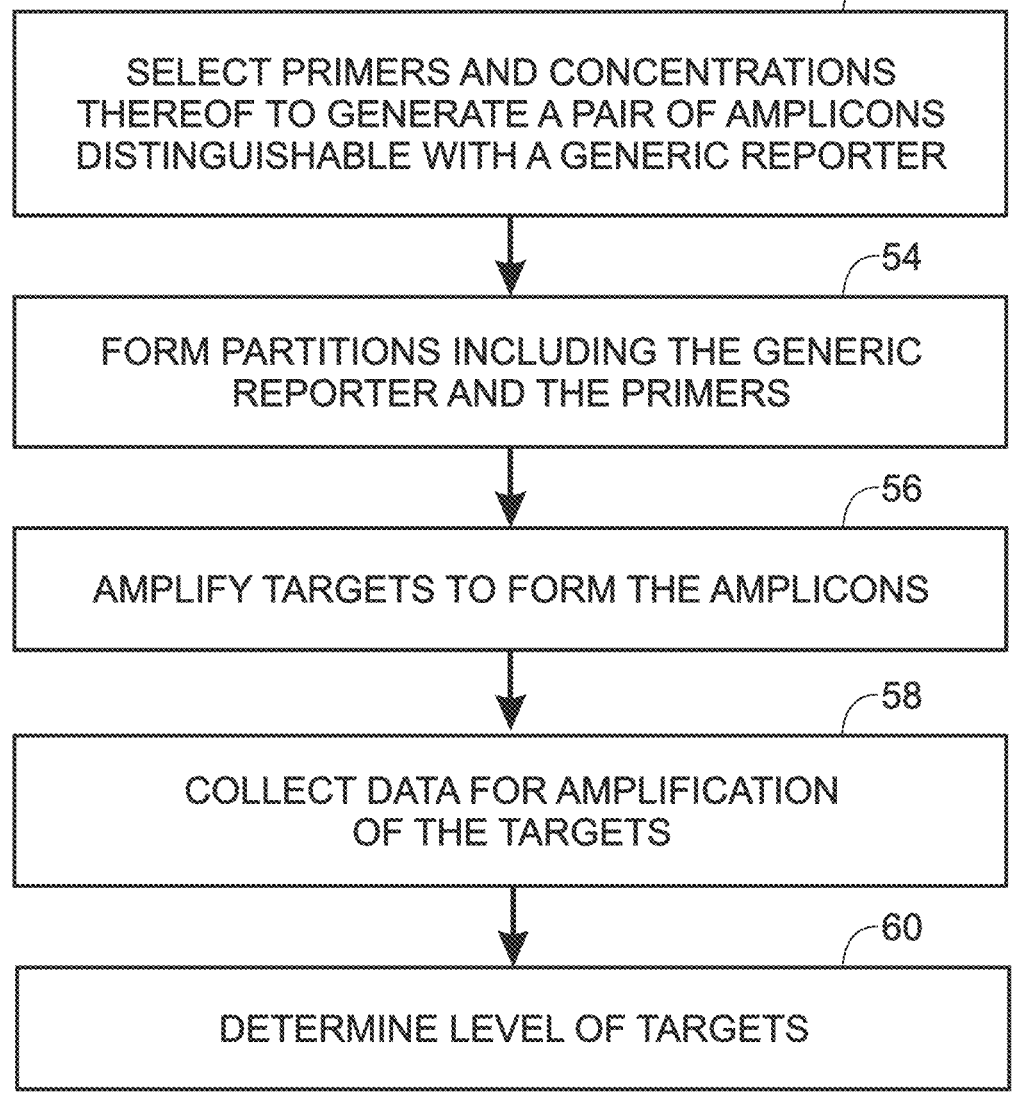
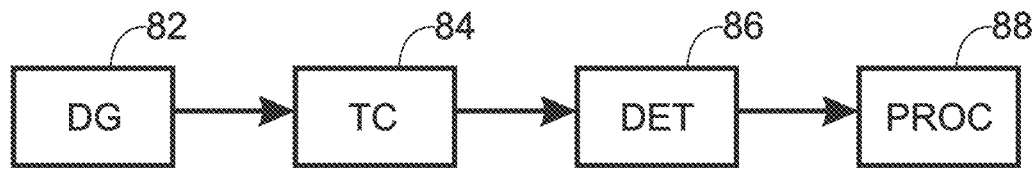

FORM PARTITIONS → AMPLIFY   DETECT

DIGITAL ASSAYS WITH A GENERIC REPORTER

CROSS-REFERENCES TO PRIORITY APPLICATIONS

This application is a continuation of U.S. patent application Ser. No. 15/973,243, filed May 7, 2018, now U.S. Pat. No. 11,377,684, which, in turn, is a divisional of U.S. patent application Ser. No. 14/191,295, filed Feb. 26, 2014, now U.S. Pat. No. 9,970,052.

The '295 application, in turn, is a continuation-in-part of U.S. patent application Ser. No. 13/973,940, filed Aug. 22, 2013, and is based upon and claims the benefit under 35 U.S.C. § 119(e) of U.S. Provisional Patent Application Ser. No. 61/789,703, filed Mar. 15, 2013, and U.S. Provisional Patent Application Ser. No. 61/864,792, filed Aug. 12, 2013. The '940 application, in turn, is based upon and claims the benefit under 35 U.S.C. § 119(e) of U.S. Provisional Patent Application Ser. No. 61/692,635, filed Aug. 23, 2012. Each of these priority patent applications is incorporated herein by reference in its entirety for all purposes.

CROSS-REFERENCES TO OTHER MATERIALS

This application incorporates herein by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; U.S. Patent Application Publication No. 2012/0152369 A1, published Jun. 21, 2012; U.S. Patent Application Publication No. 2013/0040841 A1, published Feb. 14, 2013; U.S. patent application Ser. No. 14/099,750, filed Dec. 6, 2013; U.S. patent application Ser. No. 14/171,754, filed Feb. 3, 2014; U.S. patent application Ser. No. 14/171,761, filed Feb. 3, 2014; and Joseph R. Lakowicz, PRINCIPLES OF FLUORESCENCE SPECTROSCOPY (2 nd Ed. 1999).

INTRODUCTION

Digital assays generally rely on the ability to detect the presence or activity of individual copies of an analyte in a sample. In an exemplary digital assay, a sample is separated into a set of partitions, generally of equal volume, with each containing, on average, less than about one copy of the analyte. If the copies of the analyte are distributed randomly among the partitions, some partitions should contain no copies, others only one copy, and, if the number of partitions is large enough, still others should contain two copies, three copies, and even higher numbers of copies. The probability of finding exactly 0, 1, 2, 3, or more copies in a partition, based on a given average concentration of analyte in the partitions, is described by a Poisson distribution. Conversely, the concentration of analyte in the partitions (and thus in the sample) may be estimated from the probability of finding a given number of copies in a partition.

Estimates of the probability of finding no copies and of finding one or more copies may be measured in the digital assay. Each partition can be tested to determine whether the partition is a positive partition that contains at least one copy of the analyte, or is a negative partition that contains no copies of the analyte. The probability of finding no copies in a partition can be approximated by the fraction of partitions tested that are negative (the "negative fraction"), and the probability of finding at least one copy by the fraction of partitions tested that are positive (the "positive fraction"). The positive fraction or the negative fraction then may be utilized to determine the concentration of the analyte in the partitions, such as with Poisson statistics.

Digital assays frequently rely on amplification of a nucleic acid target in partitions to enable detection of a single copy of an analyte. Amplification may be conducted via the polymerase chain reaction (PCR), to achieve a digital PCR assay. Amplification of the target can be detected optically from a fluorescent probe included in the reaction. In particular, the probe can include a fluorophore that provides a fluorescence signal indicating whether or not the target has been amplified.

A digital PCR assay can be multiplexed to permit detection of the presence of two or more different targets in the same set of partitions. Amplification of the targets can be distinguished by utilizing target-specific probes. However, such probes can be expensive and may need to be custom-synthesized, further increasing the cost.

SUMMARY

The present disclosure provides a digital assay system, including methods, apparatus, and compositions, for assay of one or more targets in a set of partitions containing a generic reporter of target amplification.

BRIEF DESCRIPTION OF THE DRAWINGS

FIG. 1 is a flowchart of an exemplary method of performing a multiplexed digital assay of at least two targets in the same set of partitions each containing primers for the targets and a generic reporter of amplification, in accordance with aspects of the present disclosure.

FIG. 2 is an exemplary system configured to perform selected aspects of the method of FIG. 1, in accordance with aspects of the present disclosure.

DETAILED DESCRIPTION

Figure 3:
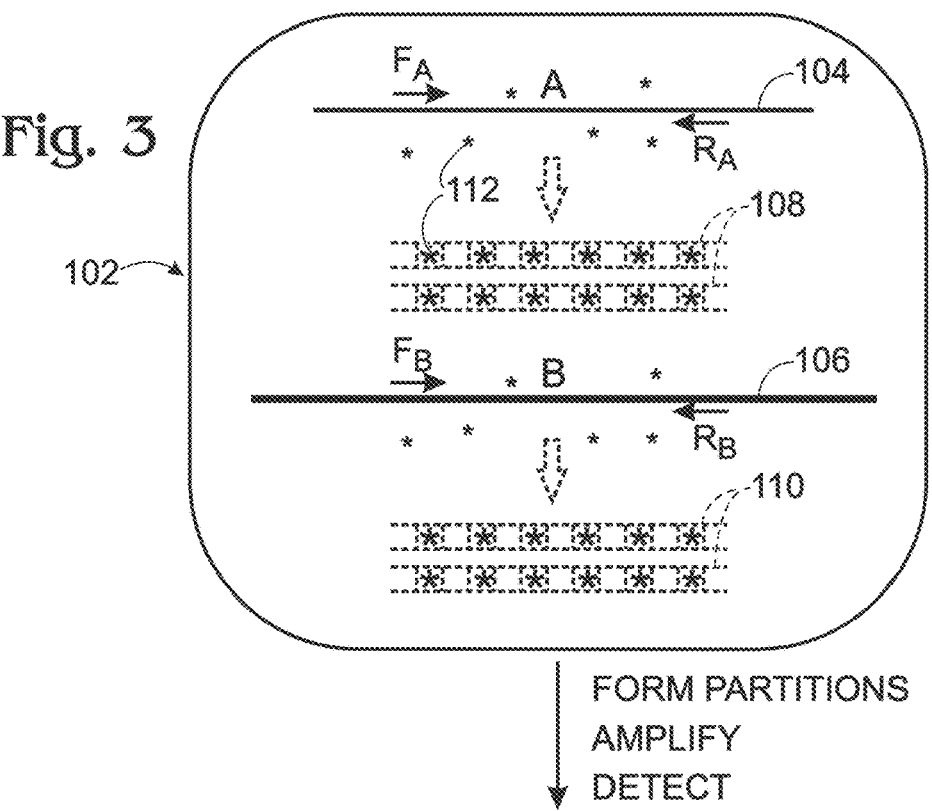
FIG. 3 is a schematic diagram illustrating selected exemplary aspects of the method of FIG. 1 performed to assay a pair of targets (targets A and B) in partitions containing a generic reporter, with the strategy for target amplification in partitions and detection with the generic reporter presented in an exemplary bulk phase from which the partitions may be formed (amplification arrows and amplicons are shown in broken lines), in accordance with aspects of the present disclosure.

The present disclosure provides a digital assay system, including methods, apparatus, and compositions, for assay of one or more targets in a set of partitions containing a generic reporter of target amplification.

An exemplary method of performing a digital assay is provided. In the method, partitions may be formed, with each partition including a portion of a same mixture. The mixture may contain a first target and a second target and also may contain a generic reporter that is sensitive to amplification of either target. Only a subset of the partitions each may contain at least one copy of the first target and only a different subset of the partitions each may contain at least one copy of the second target. The first target and the second target may be amplified in the partitions. Amplification data may be collected from the generic reporter for a plurality of the partition. Amplification of the first target in a partition may be distinguishable from amplification of the second target. A level of each target may be determined.

Another exemplary method of performing a digital assay is provided. In the method, partitions may be formed, with each partition including a portion of a same mixture. The mixture may contain a target and also may contain a generic reporter that is sensitive to amplification of the target. Only a subset of the partitions each may contain at least one copy of the target. The target and at least one byproduct may be amplified in the partitions. Amplification data may be collected from the generic reporter for a plurality of the partitions. Amplification in a partition of the target, the byproduct, or neither the target nor the byproduct may be distinguishable from one another in the data. A level of the target may be determined.

Still another method of performing a digital assay is provided. In the method, partitions may be formed, with each partition including a portion of a same mixture. The mixture may contain a target and a generic reporter that is sensitive to amplification of the target. Only a subset of the partitions each may contain at least one copy of the target. The partitions may be thermally cycled to amplify the target. Signals to be detected from the thermally cycled partitions may be stabilized by cooling the partitions below room temperature, heating the partitions above 80 degrees Celsius, and cooling the partitions again below room temperature. Amplification data from the generic reporter may be collected for a plurality of the partitions. A level of the target may be determined.

Yet another method of performing a multiplexed digital assay is provided. In the method, primers and concentrations thereof may be selected for amplification of first and second targets to generate corresponding first and second amplicons that are distinguishable with a generic reporter. Partitions may be formed, with each partition containing the generic reporter and the primers at the selected concentrations. A template for each target may be present at partial occupancy in the partitions. The first target and the second target may be amplified in the partitions. Light emitted by the generic reporter may be detected from individual partitions. A level of each target may be determined based on the light detected.

A composition for performing a multiplexed assay is provided. The composition may comprise a plurality of droplets each containing amplification reagents sufficient for amplifying a first target and a second target and also containing a generic reporter sensitive to amplification of either target. Only a subset of the droplets each may contain at least one copy of the first target and only a different subset of the droplets each may contain at least one copy of the second target. A continuous phase may surround each of the droplets.

Polymerase chain reaction (PCR) is a ubiquitous technique in biomedical research, clinical diagnostics, and forensics, among others. Those trained in the technique are familiar with various forms of multiplex PCR, including endpoint multiplexed PCR, multiplexed probe-based quantitative PCR, and dye-based multiplexing with the fluorescent dye sold under the trademark SYBR®. There are advantages and disadvantages to each of these approaches. Endpoint PCR can support high levels of multiplexing, but generally requires time-consuming gel electrophoresis to detect amplified products. Multiplexed probe-based quantitative PCR is a kinetic ("real-time") assay that, unlike endpoint PCR, does not required post-PCR processing for detection, but amplicon detection is limited by instrument capability. Commercially-available real-time PCR instruments can support use of up to four fluorophores and thus four probes, with multiplexing limited to four amplicons (one amplicon per probe). Finally, dye-based multiplexing is inexpensive, because it does not require labeled probes and is less time-consuming. However, the approach relies on melt-curve analysis to detect the various PCR products, and does not allow direct quantification of the products. Also, melt-curve analysis may not have the resolution to distinguish amplicons with similar melting temperatures. There is currently no method available for direct detection and quantification of multiple DNA targets amplified in a single tube using only a DNA intercalating dye as a reporter of amplification.

The present disclosure provides a novel approach for multiplexed PCR in partitions, such as emulsion droplets, and detection thereof with a DNA intercalating dye. The approach involves amplification, detection, and quantification of multiple DNA targets. Target amplification may be carried out in a standard PCR mixture with a DNA intercalating dye, e.g., the fluorescent dye sold under the trademark EVAGREEN®, and a number of primer pairs, such as one for each of the targets. The primer pairs may be assembled in the mixture at various different concentrations in a manner to manipulate amplicon yield for each of the targets. Based on yield, the amplified products can be distinguished according to signal amplitude detected from the intercalating dye.

An element in the strategy may be the ability to manipulate fluorescence output by varying primer concentration. Primer concentration directly affects yield and indirectly affects fluorescence of amplicon-bound dye. Primer concentration(s) for each of the targets in a multiplex reaction can be adjusted to produce a different signal amplitude for each of the various amplified targets. Amplified targets can be identified by the positions of corresponding amplitude clusters in the data and quantified by the number of partitions present in each cluster.

The method disclosed herein may allow for detection and quantification of multiple amplicons, of the same or different size, amplified in a single well, using only a DNA binding dye as the reporter. This method has advantages over conventional endpoint PCR multiplexing. For example, the method saves time: further processing of PCR products, e.g., gel electrophoresis and imaging, is not required to detect the amplicons. Alternatively, or in addition, the method can offer amplicon size independence: amplicons of similar (e.g., equal) or different lengths can be detected from the same multiplex reaction. In contrast, amplicons of similar length generally cannot be resolved by gel electrophoresis, limiting the ability to multiplex similar-sized amplicons in conventional endpoint PCR. The method disclosed herein is different from multiplexed probe-based quantitative PCR because the method can be performed without the use of sequence-specific probes, which can be significantly more expensive than an intercalating dye. The method disclosed herein is different from dye-based multiplexing with a real-time instrument. For example, amplicons can be distinguished without a melt-curve analysis.

Further aspects of the present disclosure are presented in the following sections: (I) overview of multiplexed digital assays with a generic reporter and (II) examples.

I. Overview of Multiplexed Digital Assays with a Generic Reporter

This section provides an overview of multiplexed digital assays performed with a generic reporter; see FIGS. 1-9.

FIG. 1 shows a flowchart of an exemplary method 50 of performing a multiplexed digital assay with a generic reporter. The steps presented for method 50 may be performed in any suitable order and in any suitable combination. Furthermore, the steps may be combined with and/or modified by any other suitable steps, aspects, and/features of the present disclosure, including those described in the patent documents listed above under Cross-References, which are incorporated herein by reference.

Primers and concentrations thereof may be selected to generate at least a pair of amplicons that are distinguishable with a generic reporter in partitions, indicated at 52. The generic reporter may fluoresce more brightly when bound to the amplicon, relative to being unbound or bound to single-stranded nucleic acid. Each amplicon (interchangeably termed an amplified target) may be double-stranded and may correspond to a distinct target that is amplified. The amplicons may be distinguishable from each other in partitions because each amplicon is generated with a different characteristic yield (which may be described using any suitable measure, e.g., by mass, by total combined length of amplicon, etc.). The result is a characteristic, distinct amount of the generic reporter bound to each amplicon in a partition, and distinguishable amplitudes of fluorescence detected from the bound reporter. Different yields by mass of the pair of amplicons may be generated because the pair of amplicons are of different length and/or are replicated to a different final copy number and/or mass.

The pair of amplicons may be a longer amplicon and a shorter amplicon that are amplified to about the same copy number in individual partitions. In this case, the longer amplicon generally binds more copies of the reporter than the shorter amplicon and gives a stronger fluorescence signal. In other cases, the longer amplicon may be amplified to a lower copy number than the shorter amplicon, everything else being equal.

The pair of amplicons may be similar or identical in length and amplified to different copy numbers. In this case, the more-abundant amplicon generally binds more copies of the reporter than the less-abundant amplicon and gives a stronger signal.

The number of copies of a given amplicon produced in the partitions may be varied by changing the concentration of one or more primers involved in amplification of a target to produce the amplicon. Accordingly, the concentration of one or more primers for each target may be selected to produce a suitable number of copies for the corresponding amplicon, such that reporter signals for the amplicons are distinguishable.

Each target of a multiplexed assay may be amplified by at least one primer or a pair of primers, among others. In some cases, the same primer may be involved in amplification of two or more of the targets. For example, a first target may be amplified by a forward primer and a reverse primer, and a second target may be amplified by the same forward primer and a different reverse primer or a different forward primer and the same reverse primer. In other cases, each target may be amplified with a different forward primer and a different reverse primer.

The primers and concentrations thereof may be selected based on testing performed in different sets of partitions, with a variable concentration and/or length and/or melting temperature of at least one of the primers, and/or with a variable length of at least one of the amplicons. In some examples, the concentration of only one primer for a target may be varied or of each a pair of primers for a target may be varied together. In some examples, two or more different forward primers and/or two or more different reverse primers for a target may be tested, with each different primer defining a different amplicon endpoint and thus resulting in a different amplicon size. In some cases, a different primer concentration for amplification of each target and/or primers that produce different amplicon sizes for the targets may be selected without any preliminary testing to optimize separation of partition populations in the data. For example, the primer concentrations and/or amplicon lengths may be selected based on an expected or assumed relationship between primer concentration (and/or amplicon length) and the amplitude of a corresponding amplicon signal.

A generic reporter (interchangeably termed a nonspecific reporter) binds without substantial specificity to a product of a reaction (e.g., an amplicon), such that other structurally different substances of the same class as the product (e.g., other amplicons of unrelated sequence) can also be bound by the reporter. The nonspecific binding may not depend on a unique feature of the arrangement of atoms of one or both of the reporter and the product (e.g., the target and/or amplicon). Multiple copies of the generic reporter may be capable of binding to a single copy of a reaction product, for example, with the number of copies bound being related directly, such as proportional, to the amount or length of the reaction product. For example, the generic reporter may be a photoluminescent dye that binds to nucleic acid relatively nonspecifically. The dye may not be attached to an oligonucleotide that confers substantial sequence binding specificity. The dye may be a major groove binder, a minor groove binder, an intercalator, or an external binder, among others. The dye may bind preferentially to double-stranded relative to single-stranded nucleic acid and/or may exhibit a greater change in a photoluminescence characteristic (e.g., emission intensity) when bound to double-stranded relative to single-stranded nucleic acid.

Exemplary dyes that may be suitable include luminescent cyanines, phenanthridines, acridines, indoles, imidazoles, and the like, such as DAPI (4',6-diamidino-2-phenylindole), the fluorescent dye sold as dye Hoechst 33258 dye (bisbenzimide) under the trademark HOECHST®, acridine orange (N,N,N',N'-Tetramethylacridine-3,6-diamine), etc. Exemplary intercalating dyes that may be suitable include ethidium bromide, propidium iodide, the fluorescent dye sold under the trademark EVAGREEN®, the green dye sold under the trademark SYBR® (N',N'-dimethyl-N44-[(E)-(3-methyl-1,3-benzothiazol-2-ylidene)methyl]-1-phenylquinolin-1-ium-2-yl]-N-propylpropane-1,3-diamine), the gold dye sold under the trademark SYBR® ([2-(4-{[(2Z)-3-methyl-1,3-benzoxazol-2-ylidene]methyl}quinolin-1-iump, and 7-aminoactinomycin D (7-AAD), among others.

Sample preparation. A sample may be prepared for the assay. Preparation of the sample may include any suitable manipulation of the sample, such as collection, dilution, concentration, purification, lyophilization, freezing, extraction, restriction-enzyme digestion, shearing, combination with one or more assay reagents to form a mixture (also termed a sample-containing mixture, a bulk phase, or a reaction mixture), performance of at least one preliminary reaction to prepare the sample for one or more reactions in the assay, or any combination thereof, among others. The preparation may isolate a class of analyte, such as nucleic acid that includes copies of one or more nucleic acid targets, and/or may modify and/or fragment the analyte. Preparation of the sample may include rendering the sample competent for subsequent performance of one or more reactions, such as one or more enzyme catalyzed reactions and/or binding reactions.

In some embodiments, preparation of the sample may include combining the sample with reagents to produce a sample-containing mixture for performing a reaction (such as an amplification reaction) for each target and for reporting an extent of each reaction (e.g., whether or not the reaction occurred above a threshold level or within a range). Reagents for amplification may include any combination of primers for targets, dNTPs and/or NTPs, at least one enzyme (e.g., a polymerase, a ligase, a reverse transcriptase, a restriction enzyme, or a combination thereof, among others, each of which may or may not be heat-stable), and/or the like. Accordingly, the mixture may have a complete set of reagents for (i.e., may be competent for) amplification of each target under suitable environmental conditions (e.g., incubation at an elevated temperature or modulation of temperature (such as by thermocycling)). The mixture may be capable of amplification of each of one or more targets, if present, in the sample (or a partition thereof). Reagents for reporting may include at least one generic reporter. A single generic reporter may be used that is sensitive to amplification of each target and may have a luminescence that varies according to whether or not amplification of a given target has occurred. Preparation of the mixture may render the sample capable of reporting, or being analyzed for, whether or not a reaction, such as amplification, has occurred, on a target-by-target basis, and optionally the extent of any such reaction.

In some embodiments, preparation of the sample may include combining the sample with reagents for performance of at least two assays, such as two amplification assays. The reagents thus may include primers for amplification and one or more detectable reporters to report whether or not amplification occurred. Reagents for amplification may include any combination of primers, dNTPs and/or NTPs, at least one enzyme (e.g., a polymerase, a ligase, a reverse transcriptase, a restriction enzyme, or a combination thereof, each of which may or may not be heat-stable), and/or the like. Accordingly, preparation of the sample may render the sample (or partitions thereof) capable of amplification of each target, if present, in the sample (or a partition thereof). Reagents for reporting may or may not include a different reporter for each target of interest. Accordingly, preparation of the sample for reporting may render the sample capable of reporting, or being analyzed for, whether or not amplification has occurred, on a target-by-target basis, and optionally the extent of any such amplification. The same generic reporter may report amplification of each target. The generic reporter may be a single compound or a mixture of compounds.

The term "luminescence" means emission of light that cannot be attributed merely to the temperature of the emitting body. Exemplary forms of luminescence include photoluminescence, chemiluminescence, electroluminescence, or the like. A "luminophore" is any atom or associated group of atoms capable of luminescence. Photoluminescence is any luminescence produced in response to irradiation with excitation light and includes fluorescence, phosphorescence, etc. Accordingly, a luminophore may be a fluorophore or a phosphor, among others.

A target interchangeably may be termed an analyte, a species, or, in some cases, a template.

Partition formation. Partitions may be formed that include the generic reporter and the primers at the concentrations selected, indicated at 54. Portions of a same sample-containing mixture may be disposed in partitions, to form partitions for assay of at least one or at least a pair of targets. The targets may be linked targets amplified from the same template, such as from a single copy of the template, or may be unlinked targets amplified from different templates in the sample.

Each partition may include a portion of a same mixture. In some cases, the portion may constitute the entire partition. The mixture may contain each target (e.g., provided by a same sample), a generic reporter, and/or one or more amplification reagents (e.g., a complete set of reagents for amplification of each target). Accordingly, the partitions, collectively, may contain a plurality of targets and each partition may contain the same generic reporter.

Targets may or may not be associated with one another when partitions are formed. Associated targets may be linked, namely, attached to each other covalently and/or by base pairing. In other cases, associated targets may be held in the same compartment (e.g., the same biological cell). Targets that are "associated" have a significant connection to each other in the sample, such as having a degree of association (e.g., linkage) of at least about 10%, 25%, 50%, 80%, 90%, or about 100% in the sample immediately before and/or during partition formation. The degree of association of targets may be assumed or expected. The degree of association indicates the frequency with which linked targets distribute together to the same partitions in a concentration-independent manner. Targets that occupy the same partition, whether due to association of the targets with each other or random chance, may be described as being co-localized or coincident in the partition. Targets that have a high degree of association (e.g., linkage) are co-localized to the same partitions at a corresponding high frequency, whether the targets are abundant or rare in the sample. For example, targets that have 90% linkage should co-localize in at least 90% of the partitions that contain one of the targets. In contrast, targets that have no linkage should co-localize according to the product of the probabilities of finding each target in a given partition, which increases with the concentration of the targets.

The partitions when provided (e.g., when formed) may contain each target at "partial occupancy," which means that each partition of only a subset of the partitions contains at least one copy of each target (and/or template) to be assayed. For example, with a multiplexed assay performed on a first target and a second target, only a first subset of the partitions contains the first target, and only a second subset of the partitions contains the second target. The first subset and the second subset of the partitions may be the same subset, if the first target and the second target are fully associated with each other when the partitions are formed. Alternatively, the first subset and the second subset of the partitions may be different if the first target and the second target are not fully associated with each other when the partitions are formed. In some cases, if the targets are not fully associated, each partition of a different third subset of the partitions may contain at least one copy of each target. Accordingly, with partial occupancy, one or more (e.g., a plurality) of the partitions contain no copies of the first target, one or more (e.g., a plurality) of the partitions may contain a single copy (only one copy) of the first target, and, optionally, yet one or more of the partitions (e.g., the rest of the partitions) may contain two or more copies of the first target. Similarly, with partial occupancy, one or more (e.g., a plurality) of the partitions contain no copies of the second target, one or more (e.g., a plurality) of the partitions may contain a single copy (only one copy) of the second target, and, optionally, yet one or more of the partitions (e.g., the rest of the partitions) may contain two or more copies of the second target.

The term "partial occupancy" is not restricted to the case where there is no more than one copy of a particular template/target of interest in any partition. Partitions containing a template and/or a target at partial occupancy may, for example, contain an average of more than, or less than, about one copy, two copies, or three copies, among others, of the template/target per partition when the partitions are provided or formed. Copies of a template (and/or target) may have a random distribution among the partitions, which may be described as a Poisson distribution. In some cases, a significant number of the partitions (e.g., at least about 1%, 2%, 5%, 10%, or 20%, among others, of the partitions) may contain a copy of each of at least two targets, and/or a plurality of the partitions each may contain at least one copy of all targets.

Partition formation may involve distributing or separating portions of a sample-containing bulk phase into partitions.

Any suitable fraction including up to all of the bulk phase may be distributed to the partitions. Each partition may be and/or include a fluid volume that is isolated from the fluid volumes of other partitions. The partitions may be isolated from one another by a fluid/liquid phase, such as a continuous phase of an emulsion, by a solid phase, such as at least one wall of a container, or a combination thereof, among others. In some embodiments, the partitions may be droplets disposed in a continuous phase, such that the droplets and the continuous phase collectively form an emulsion.

The partitions may be formed by any suitable procedure, in any suitable manner, and with any suitable properties. For example, the partitions may be formed with a fluid dispenser, such as a pipette, with at least one droplet generator having an orifice at which droplets are created, by agitation of the sample (e.g., shaking, stirring, sonication, etc.), and/or the like. Accordingly, the partitions may be formed serially, in parallel, or in batch. The partitions may have any suitable volume or volumes. The partitions may be of substantially uniform volume or may have different volumes. Exemplary partitions having substantially the same volume are monodisperse droplets. Exemplary volumes for the partitions include an average volume of less than about 100, 10 or 1 µL, less than about 100, 10, or 1 nL, or less than about 100, 10, or 1 µL, among others.

Partitions competent for amplification of each target may be formed directly from a bulk phase containing the template, or may be formed in multiple steps. In some cases, the step of forming partitions may include dividing a bulk phase into isolated fluid volumes (such as droplets) containing the targets at partial occupancy. The fluid volumes may be the partitions themselves or may contribute to the partitions. For example, the fluid volumes may be a first set of fluid volumes, and the step of forming partitions may include combining individual fluid volumes of the first set with individual fluid volumes of a second set. The second set may include one or more reagents for amplification of one or more of the targets, such as at least one primer for amplification of at least one of the targets, primers for a pair of targets, or the like. The step of combining may include fusing fluid volumes of the first set individually with fluid volumes of the second set, such as fusing droplets containing the targets with droplets containing primers for amplification of one or more of the targets.

The targets may be amplified in the partitions to form the amplicons, indicated at 56. Amplification of each target may occur selectively (and/or substantially) in only a subset of the partitions, such as less than about three-fourths, one-half, one-fourth, or one-tenth of the partitions, among others. Amplification of each target may occur selectively in partitions containing at least one copy of the target (i.e., containing at least one copy of a template corresponding to the target). Amplification may be linear or exponential, among others.

Amplification may or may not be performed isothermally. In some cases, amplification in the partitions may be encouraged by heating the partitions and/or incubating the partitions at a temperature above room temperature, such as at a denaturation temperature, an annealing temperature, and/or an extension temperature, for one or a plurality of cycles. In some examples, the partitions may be thermally cycled to promote a polymerase chain reaction and/or ligase chain reaction. Exemplary isothermal amplification approaches that may be suitable include nucleic acid sequence-based amplification, transcription-mediated amplification, multiple-displacement amplification, strand-displacement amplification, rolling-circle amplification, loop-mediated amplification of DNA, helicase-dependent amplification, and single-primer amplification, among others.

Data collection. Amplification data may be collected, indicated at 58. The data may be collected by detecting light from individual partitions, such as detecting light emitted by the generic reporter present in individual partitions. The light may be emitted in response to irradiation of the partitions with excitation light. The data may be collected for emission of light from the partitions in one waveband (one optical channel), a pair of wavebands (two optical channels), or the like.

R targets may be assayed in a multiplexed assay, and the data may be collected in less than R optical channels (e.g., in different wavelength regimes). In other words, the number (R) of targets assayed may be greater than the number of optical channels used for detecting the target-specific reactions. In some cases, the data may be collected in only one or two optical channels, or in at least two, three, or more optical channels, among others. In some cases, data may be collected from the same number of optical channels as targets in the assay. An optical channel interchangeably may be termed a detection channel.

An optical channel may represent a particular detection regime with which emitted light is generated and detected. The detection regime may be characterized by a spectral content (i.e., a wavelength regime) for detection of emitted light. If pulsed excitation light is used in the detection regime to induce light emission, the detection regime may be characterized by a spectral content (a wavelength(s) or waveband(s)) for illumination with excitation light and/or a time interval during which light emission is detected with respect to each light pulse. Accordingly, optical channels that are different from each other may differ with respect to the spectral content (wavelength(s)/waveband(s)) of excitation light, with respect to the spectral content (wavelength(s)/waveband(s)) of emitted light that is detected, and/or with respect to the time interval during which emitted light is detected relative to each pulse of excitation light, among others.

Data collection may include generating one or more signals representative of light detected from individual partitions. The signals may represent an aspect of light, such as an intensity, lifetime, polarization, etc. The signals optionally may include data collected in two or more different optical channels (e.g., in different wavelength ranges (wavebands) and/or color regimes) from reporters for the same and/or different targets). The light detected from each reporter may be light emitted from a luminophore (e.g., a fluorophore). The light detected in a given channel may be detected such that light from the reporter bound to different amplicons is summed or accumulated without attribution to a particular amplicon. Thus, the signals for a given channel may represent two, three, four, or more assays and thus two, three, four, or more targets. In other cases, the signals for two or more of the targets may be detected in different optical channels.

The signal(s) may be created based on light detected from a generic reporter in the partitions. The reporter may report whether at least one of two or more particular amplification reactions represented by the signal has occurred in a partition and thus whether at least one copy of at least one of two or more particular targets corresponding to the two or more particular amplification reactions is present in the partition. The level or amplitude of the signal corresponding to the reporter may be analyzed to determine whether or not at least one of the particular amplification reactions has occurred and at least one copy of one of the particular targets is present. The level or amplitude of the signal may vary among the partitions according to whether at least one of the particular amplification reactions occurred or did not occur and at least one of the particular targets is present or absent in each partition. For example, a partition classified as positive for a particular target may produce a signal value that is above a given threshold and/or within a given range. Partitions may be analyzed and signals created at any suitable time(s). Exemplary times include at the end of an assay (endpoint assay), when reactions have run to completion and the data no longer are changing, or at some earlier time, as long as the data are sufficiently and reliably separated.

Data may be collected from a plurality of the partitions (i.e., only a subset or all of the partitions) under any suitable conditions. All of the data may be collected at about the same temperature from the plurality of partitions, at a temperature that is below a melting temperature of each amplicon, below an annealing temperature used in thermocycling for amplification, and/or below about 50 or 45 degrees Celsius, among others. The amplification data may be collected after an endpoint of amplification has been reached for each target.

Population identification. Partition populations (interchangeably termed clusters or bands) that are negative for both targets, positive for only one of the targets (single positives), and positive for combinations of targets (double positives, etc.) may be identified from the data. Identification may be performed by a data processor using an algorithm (e.g., an algorithm that identifies patterns (e.g., partition clusters) in the data), by a user, or a combination thereof. In some cases, a data processor may produce and output (e.g., display) a plot of the collected data (e.g., a 2-D scatter plot or histogram). The user then may define the boundary of each population based on the plot(s), e.g., through a graphical user interface to define population boundaries, and/or by inputting values (e.g., representing amplitude thresholds/ranges) to define a boundary for each population. Each population boundary may be defined by one or more ranges of values, a geometrical shape that surrounds the population (e.g., a polygon, ellipse, etc.), or the like.

Identification of partition populations may include assigning each partition to one of a plurality of predefined bins each corresponding to a distinct partition population. The predefined bins may represent all possible combinations of negatives and positives for the targets.

The reaction components and/or conditions of any of the assays disclosed herein may be adjusted to improve the resolution of different partition populations in the data. By changing the concentration of a particular assay within a multiplexed assay, the reaction efficiency for a particular target can be affected, which may result in a difference in signal level that allows populations detected with the same reporter to be distinguished from one another. By changing reaction components/conditions, additional targets may be detected in the same multiplexed assays. In some cases, the signal amplitude for a target may be adjusted by varying the concentration of one or both primers for the target. Varying primer concentration without changing the reporter concentration may be useful in assays where the same generic reporter is used to detect two or more targets, but each of the two targets is amplified with at least one different primer. In some cases, the signal amplitude for one or more targets may be adjusted by changing the annealing temperature used for thermocycling, the total concentration of dNTPs, the amounts of individual dNTPs relative to each other (e.g., if the two targets have substantially different base compositions), the melting temperature of one or more primers (e.g., by the changing primer length and/or GC content), the concentration of the generic reporter, or any combination thereof, among others.

Partitions positive for each target (or reaction byproduct) may have a different (and distinguishable) signature in the collected amplification data. The signature may be a characteristic average value or range for one or more types of signals (e.g., collected in one or more optical channels) from partitions containing the target.

Obtain partition counts. A partition count for each partition population/cluster may be obtained. The partition count may be a value representing the number of partitions constituting a particular partition population/cluster.

Determination of target levels. A level of each target may be determined based on the collected data, indicated at 60. Determination of target levels may (or may not) be based on each target having a Poisson distribution among the partitions. Each level may, for example, be a value representing the total number of partitions positive for the target, or a concentration value, such as a value representing the average number copies of the target per partition. The partition data further may be used (e.g., directly and/or as concentration data) to estimate copy number (CN) and copy number variation (CNV), using any suitable algorithms.

A level (e.g., a concentration) of each target may be determined with Poisson statistics. The concentration may be expressed with respect to the partitions or a unit volume, and/or with respect to a sample providing the target, among others. The concentration of the target in the partitions may be calculated from the fraction of partitions that are positive for the target (or, equivalently, the fraction of partitions that are negative for the target) by assuming that copies of the target (before amplification) have a Poisson distribution among the partitions. With this assumption, the fraction f(k) of partitions having k copies of the target is given by the following equation:

$$f(k) = \frac{c^k}{k!} e^{-c} \tag{1}$$

Here, C is the concentration of the target in the partitions, expressed as the average number of target copies per partition (before amplification). Simplified Poisson equations may be derived from the more general equation above and may be used to determine target concentration from the fraction of positive partitions. An exemplary Poisson equation that may be used is as follows:

$$C = -\ln\left(1 - \frac{N_+}{N_{tot}}\right) \tag{2}$$

where $N_+$ is the number of partitions (i.e., the partition count) positive for a given target, and where $N_{tot}$ is the total number of partitions that are positive or negative for the target. $N_{tot}$ is equal to a sum of (a) $N_+$ for the target and (b) the number of partitions negative for the target, or $N_-$. $N_+/N_{tot}$ (or $N_+/(N_++N_-)$) is equal to $f_+$, which is the fraction of partitions positive for the target (i.e., $f_+=f(1)+f(2)+f(3)+\ldots$) (see Equation 1), and which is a measured estimate of the probability of a partition having at least one copy of the target. Another exemplary Poisson equation that may be used is as follows:

$$C = -\ln\left(\frac{N_-}{N_{tot}}\right) \qquad (3)$$

where $N_-$ and $N_{tot}$ are as defined above. $N_-/N_{tot}$ is equal to $f_-$, which is the fraction of negative partitions (or $1-f_+$), is a measured estimate of the probability of a partition having no copies of the target, and C is the target concentration as described above.

Equations 2 and 3 above can be rearranged to produce the following:

$$C = \ln(N_{tot}) - \ln(N_{tot} - N_+) \qquad (4)$$

$$C = \ln(N_{tot}) - \ln(N_-) \qquad (5)$$

The concentration of each target in a multiplexed assay can, for example, be determined with any of Equations 2 to 5, using values (i.e., partition counts) obtained for $N_{tot}$ and $N_-$ or $N_+$, for each target. In some cases, the value used for $N_{tot}$ (the total partition count) may be the same for each target. In other cases, the value used for $N_{tot}$ may vary, such as if some of the populations are excluded from the total count due to population overlap. In some embodiments, $N_{tot}$ may be equivalent to a combination of all populations, namely, a sum of the partition counts for all populations identified.

The value used for $N_-$ or $N_+$ is generally different for each target, and may result from summing the counts from a plurality of partition populations each containing a different combination of the targets being tested in the multiplexed assay. For example, with three targets (A, B, and C) in a multiplexed assay, the number of partitions positive for target A, $N_{+A}$, may be calculated as the sum of counts from the single (A only), double (AB and AC), and triple (ABC) positive populations, for use in Equation 2 or 4. Equivalently, the number of partitions negative for target A, $N_{-A}$, may be calculated, for use in Equation 3 or 5, as the difference between $N_{tot}$ and $N_{+A}$. Alternatively, the number of partitions negative for A may be calculated as the sum of counts from each population that is negative for target A, namely, in this example, a triple negative ("empty") population, two single positive populations (B and C), and one double positive population (BC). The same process may be repeated for each of the other targets using partition counts from the appropriate subset of populations.

In some embodiments, an estimate of the level (e.g., concentration) of the target may be obtained directly from the positive fraction, without use of Poisson statistics. In particular, the positive fraction and the concentration (copies per partition) converge as the concentration decreases. For example, with a positive fraction of 0.1, the concentration is determined with Equation 2 to be about 0.105, a difference of only 5%; with a positive fraction of 0.01, the concentration is determined to be about 0.01005, a ten-fold smaller difference of only 0.5%. However, the use of Poisson statistics can provide a more accurate estimate of concentration, particularly with a relatively higher positive fraction, because the equation accounts for the occurrence of multiple target copies per partition.

FIG. 2 shows an exemplary system 80 for performing the digital assay of FIG. 1. System 80 may include a partitioning assembly, such as a droplet generator 82 ("DG"), a thermal incubation assembly, such as a thermocycler 84 ("TC"), a detection assembly (a detector) 86 ("DET"), and a data processing assembly (a data processor) 88 ("PROC"), or any combination thereof, among others. The data processing assembly may be, or may be included in, a controller that communicates with and controls operation of any suitable combination of the assemblies. The arrows between the assemblies indicate movement or transfer of material, such as fluid (e.g., a continuous phase of an emulsion) and/or partitions (e.g., droplets), or signals/data, between the assemblies. Any suitable combination of the assemblies may be operatively connected to one another, and/or one or more of the assemblies may be unconnected to the other assemblies, such that, for example, material/data are transferred manually.

Detector 86 may provide a plurality of optical channels in which data can be collected. The detector may have a distinct sensor or detection unit for each optical channel.

System 80 may operate as follows. Droplet generator 82 may form droplets disposed in a continuous phase. The droplets may be cycled thermally with thermocycler 84 to promote amplification of targets in the droplets. Signals may be detected from the droplets with detector 86. The signals may be processed by processor 88 to determine droplet counts (numbers of droplets) and/or target levels, among others. The system also may include a program, optionally residing on a computer-readable storage medium, for controlling any suitable aspects of a method of performing a digital assay. For example, the computer program may comprise instructions for causing the droplet generator to form droplets, the thermocycler to promote target amplification, the detector to collect data, the processor to process the collected data, or any combination thereof, among others.

Further aspects of sample preparation, assay design, partition formation, data collection, population identification, obtaining partition counts, and target level determination, among others, that may be suitable for the system of the present disclosure are described elsewhere in the present disclosure, and in the references identified above in the Cross-References, which are incorporated herein by reference.

FIG. 3 shows a schematic diagram illustrating selected exemplary aspects of the method of FIG. 1 performed to assay a pair of targets (targets A and B) in partitions containing a generic reporter. At least one bulk phase 102 (or two or more bulk phases) may be divided into fluid volumes that directly (or in combination) form partitions, such as droplets. Bulk phase 102 contains copies of at least one template (e.g., a nucleic acid template), such as templates 104, 106, that are distributed to the partitions at partial occupancy. The templates are drawn here with distinct line weights to indicate that they are different from each other in sequence. In other cases, both targets may be amplified from the same template or related versions of the template (e.g., templates representing different alleles). The template(s) may be double-stranded or single-stranded, among others. Each template may be uniform or variable in length.

The strategy for amplification of targets A and B to form respective amplicons 108, 110 is presented in bulk phase 102, even though this process generally occurs predominantly or exclusively after formation of partitions. Accordingly, amplification and products thereof are illustrated in bulk phase 102 in broken lines.

The size of each amplicon 108, 110 may be defined by at least one primer used for amplification. For example, here, a pair of primers is used for amplification of target A, namely, a forward primer ($F_A$) and a reverse primer (RA), to determine the region of template 104 that is amplified, to define the endpoints of the target and amplicon 108. Similarly, a pair of primers is used for amplification of target B, namely, a forward primer ($F_B$) and a reverse primer ($R_B$), to determine the region of template 106 that is amplified, to define the endpoints of the target and amplicon 110. Amplification of both targets may be reported by a generic reporter 112. The generic reporter is shown here bound selectively to amplicon relative to the template. However, the generic reporter may (or may not) bind with equal affinity to both.

The assay configuration of FIG. 3 forms amplicons 108, 110 of equal size, using the same concentration of primers, and with the same yield. Accordingly, the amplicons are not distinguishable based on the amplitude of the signal detected from generic reporter 112.

Figure 4:
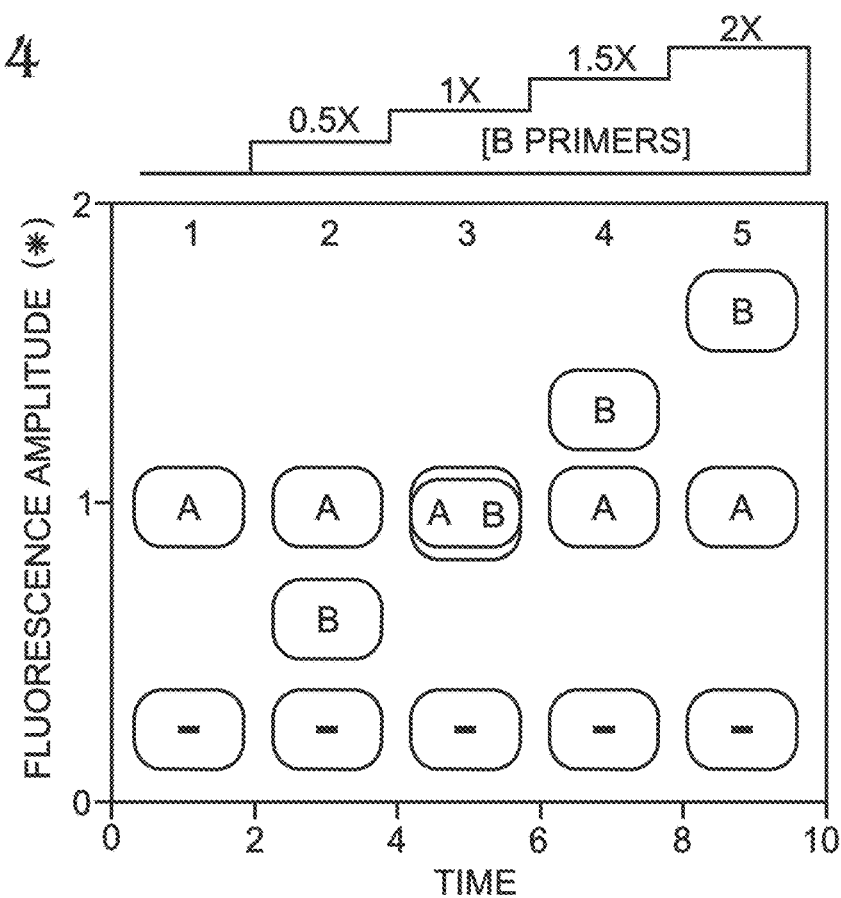
FIG. 4 is a graph of exemplary data including fluorescence amplitude (e.g., fluorescence intensity (int.)) that may be collected from separate sets of partitions (lanes 1-5) assayed for targets A and B as in FIG. 3, with a different concentration of the target B primers ($F_B$ and $R_B$) present in each set and with each band of partitions identified in the graph, in accordance with aspects of the present disclosure.

FIG. 4 shows a graph of exemplary data including signal amplitude (e.g., fluorescence intensity (int.)) that may be collected from separate sets of partitions (lanes 1-5) assayed in series for targets A and B. The assays of FIG. 4 are performed generally according to the strategy of FIG. 3, with droplets as the partitions, and with a variable concentration of the target B primers ($F_B$ and $R_B$) present in each set of partitions. Each band of droplets (interchangeably termed a cluster or population of partitions/droplets) is identified in the graph according to target content, namely, negative for both targets (−), positive for the A target (A), and positive for the B target (B). Partitions, if any, positive for both targets (AB) are not shown here and are addressed below. The units for fluorescence intensity and time are arbitrary. However, in some embodiments, the units for time may be seconds or minutes, among others, and the number of partitions represented by the data for each set in the graph may be at least $10^2$, $10^3$, $10^4$, or $10^5$, among others.

The concentration of target B primers present in each set of partitions is shown above the graph, and indicates the concentrations of the primers relative to the target A primers. Accordingly, lane 3 has equal concentrations of the primers (1X) for both targets and represents the configuration shown in FIG. 3. Bands for partitions containing amplified target A or amplified target B overlap in this case and do not permit an accurate determination of partition counts for targets A and B individually. In contrast, using less (one-half the concentration) (lane 2) or more (twice the concentration) (lanes 3 and 4) of the target B primers separates the B-positive band from the A-positive band, which allows the level of each target to be determined separately based on the partition count for each resolved band (e.g., using Equation 5 above for each target). Only two targets are shown here, but one or more additional targets also may be assayed in the same partitions.

Figure 5:
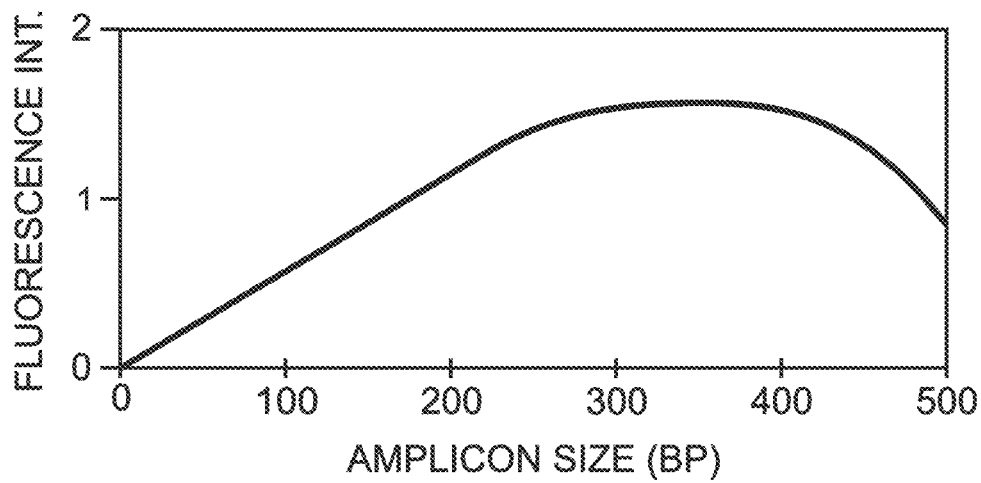
FIG. 5 is a graph of an exemplary relationship between amplicon size in a partition and fluorescence intensity (int.) measured from the partition, in accordance with aspects of the present disclosure.

FIG. 5 shows a graph of an exemplary relationship between amplicon size/length in a partition and fluorescence intensity (int.) that may be measured from the partition. The graph may be based on the assumption that the primers for the various sizes of amplicon have the same melting temperature ($T_m$) for binding to template. The fluorescence intensity is given in arbitrary units and the amplicon size is in base pairs (bp). The concentration of primers used to generate the various amplicon sizes may be held constant.

The fluorescence intensity may be positively correlated with amplicon size for shorter amplicons. For example, a linear relationship is shown here, with a 200 bp amplicon generating twice the fluorescence intensity of a 100 bp amplicon. As the amplicon size increases further, the efficiency of amplification may begin to decrease in direct relation to amplicon size, as shown by a change in slope of the curve from positive to negative. Accordingly, as shown here, the fluorescence intensity may be positively (directly) correlated with amplicon length below a first threshold length, and may be negatively (inversely) correlated with amplicon size for longer amplicons above a second threshold length. Also, amplification of longer targets to produce longer amplicons may be masked by amplification of shorter targets to produce shorter amplicons, if both are present in the same partition. Further aspects of approaches for addressing target masking are disclosed in U.S. Provisional Patent Application Ser. No. 61/759,772, filed Feb. 1, 2013, which is incorporated herein by reference. In any event, primers and thus one or more amplicon lengths may be selected for one or more of the targets based on an expected or assumed relationship between amplicon size and fluorescence intensity, such as based on any suitable aspect of the relationship shown in FIG. 5.

Primers also or alternatively may be selected based on the expected (e.g., predicted or measured) melting temperature of the primers for binding to template. For example, primers that have a lower (or higher) melting temperature may be selected to decrease (or increase) amplification efficiency and thus the amplitude of the detected signal for a given target. The melting temperature may be selected or adjusted based on the length of the primers, the GC content of the primer, the use of non-standard nucleotides (e.g., inosine) and/or nucleotide analogs, or a combination thereof, among others. In some cases, the melting temperature may be predicted based on the number of base pairs formed by a primer with the template (and/or amplicon therefrom), the number of AT base pair, the number of GC base pairs, or any combination thereof.

In some embodiments, the annealing temperature used for thermocycling may be selected or varied to establish or increase a difference in amplitude between signals for different targets. For example, a target amplified with primers that melt at a lower temperature may be more sensitive to an increase in annealing temperature than another target amplified with primers that melt at a higher temperature.

Figure 6:
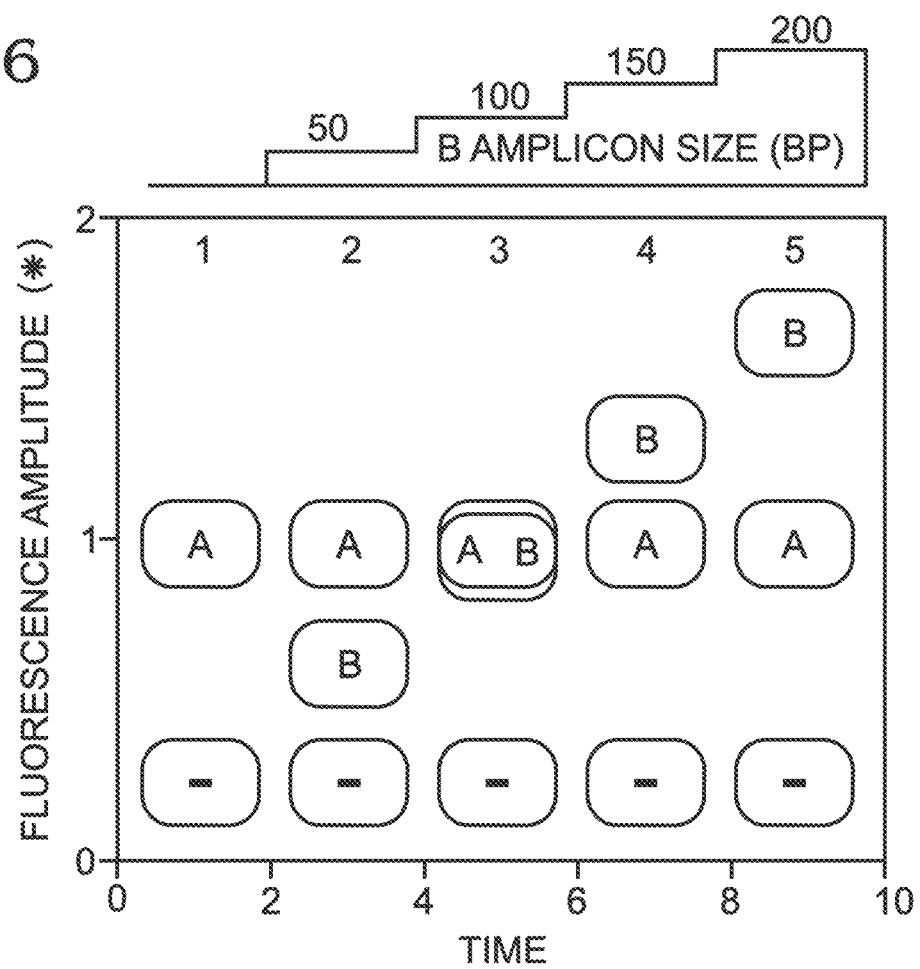
FIG. 6 is a graph of exemplary data including fluorescence amplitude (e.g., fluorescence intensity) that may be collected from separate sets of partitions (lanes 1-5) assayed for targets A and B as in FIG. 3, with a different amplicon size generated for target B in each set and with each band of partitions identified in the graph, in accordance with aspects of the present disclosure.

FIG. 6 shows a graph of exemplary data including signal amplitude (e.g., fluorescence intensity) that may be collected from separate sets of droplets (lanes 1-5) assayed for targets A and B as in FIGS. 3 and 4, but with a different amplicon size generated for target B in each set. Primers and thus one or more amplicon lengths may be selected for one or more of the targets based on tests performed with different primers and amplicon lengths, as in FIG. 6.

Figure 7:
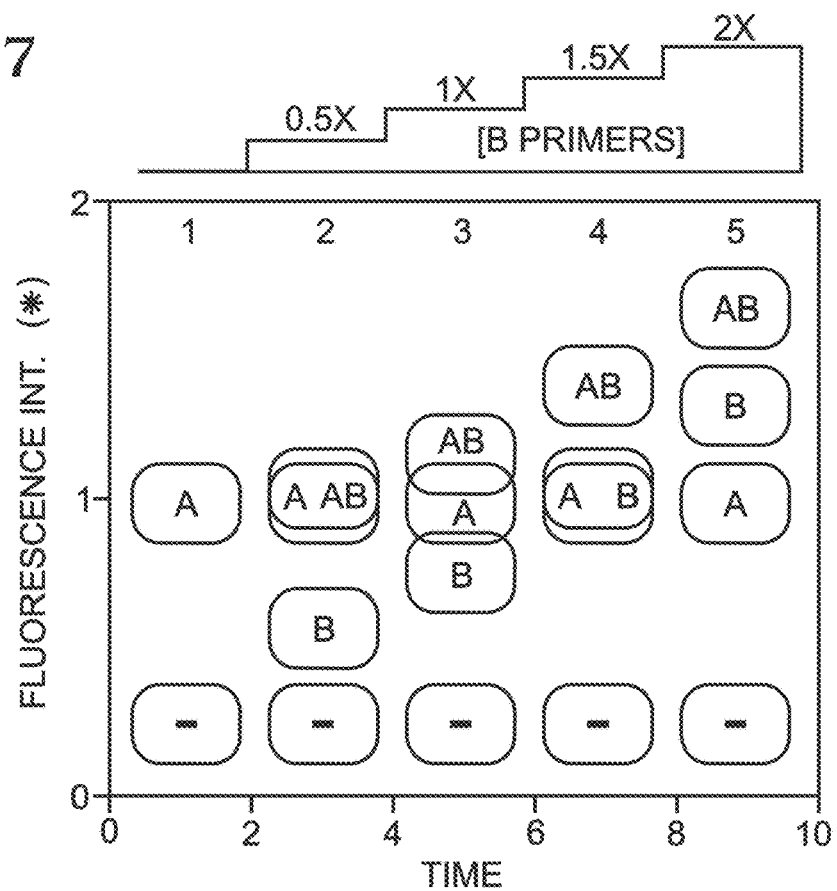
FIG. 7 is a graph of exemplary data collected and presented as in FIG. 4, but with a significant number of partitions being positive for both targets, in accordance with aspects of the present disclosure.

FIG. 7 shows a graph of exemplary data collected and presented as in FIG. 4, but with a significant number of partitions being positive for both targets (AB). The concentration of one or more primers and/or the length of one or more amplicons may be selected to resolve a double-positive partition from one or more single-positive partitions. For example, in lane 5, the double-positive AB band is resolved from both the A-only band and the B-only band, which in turn are resolved from each other.

Accordingly, the assay conditions of lane 5 permit the levels of targets A and B to be determined when there is a significant fraction of double-positive partitions. In other cases, the template concentrations (e.g., the amount of sample) may be reduced to minimize the occurrence of double-positive partitions, which may permit such double-positive partitions, if any, to be ignored without unacceptably degrading the accuracy of the assay.

Figure 8:
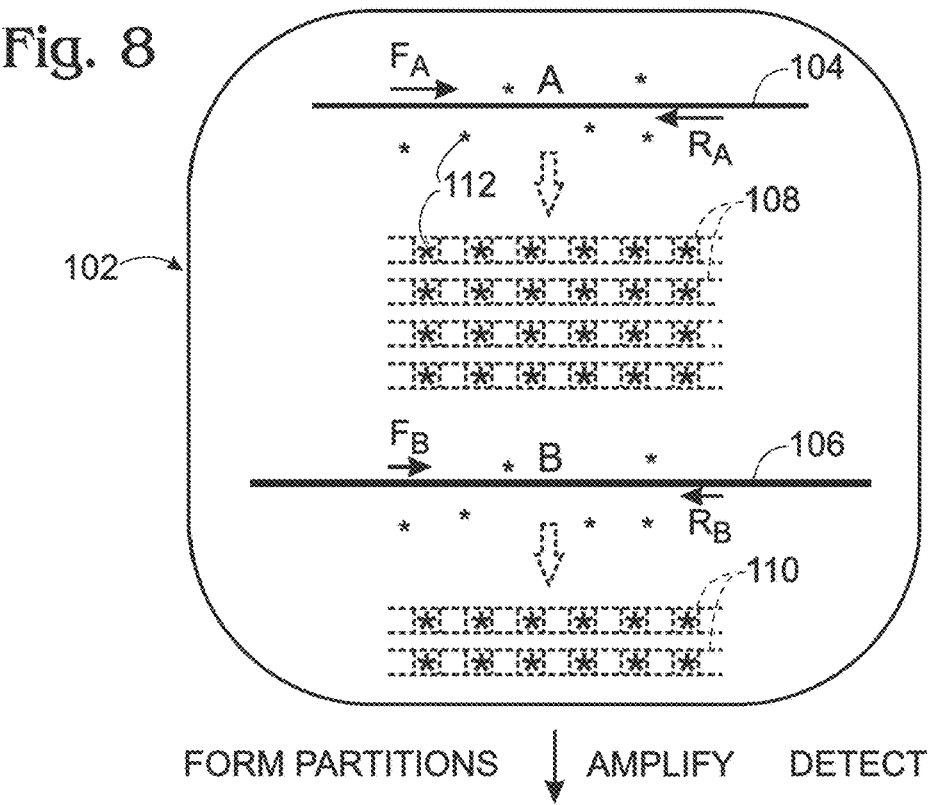
FIG. 8 is another schematic diagram illustrating selected exemplary aspects of the method of FIG. 1 performed to assay a pair of targets (targets A and B) in partitions with the same generic reporter, with the diagram constructed generally as in FIG. 3 and showing the use of primers having different melting temperatures to generate amplicons of the same length for the pair of targets, but at different efficiencies that result in different amplicon yields, in accordance with aspects of the present disclosure.

FIG. 8 shows another schematic diagram illustrating additional selected exemplary aspects of the method of FIG. 1 performed to quantify a pair of targets (targets A and B) in partitions containing a generic reporter. The diagram of FIG.

8 uses the same conventions as FIG. 3. At least one bulk phase 102 (or two or more bulk phases) may be divided into fluid volumes that directly (or in combination) form partitions, such as droplets. Bulk phase 102 contains copies of at least one template (e.g., a nucleic acid template), such as templates 104, 106, that may be distributed to the partitions at partial occupancy. The templates are drawn here with distinct line weights to indicate that they are different from each other in sequence. In other cases, both targets may be amplified from the same template or related versions of the template (e.g., templates representing different alleles). The template(s) may be double-stranded or single-stranded, among others. Each template may be uniform or variable in length.

The strategy for amplification of targets A and B to form respective amplicons 108 and 110 is presented in bulk phase 102, even though this process generally occurs predominantly or exclusively after formation of partitions. Amplification and products thereof are illustrated in bulk phase 102 with dashed lines. The relative number of copies of amplicons 108 and 110 that are generated in an average partition containing a copy of one of the templates is indicated schematically. More particularly, amplification of target A is more efficient than target B in the depicted embodiment, even though amplicons 108 and 110 may have about (or exactly) the same length. As a result, the more-efficient amplification of target A produces a greater number of copies of amplicon 108 in a positive partition than the number of copies of amplicon 110 produced by the less-efficient amplification of target B in a positive partition. Accordingly, partitions positive for target A have a stronger signal (e.g., a greater luminescence amplitude) on average than partitions positive for target B, because a larger amount of the reporter is bound to amplicon in A-positive partitions relative to B-positive partitions. The strategy shown here may be extended to perform a multiplexed assay for any suitable number of targets such as three or more targets in the same set of partitions.

The primers for amplification of the targets may be selected (e.g., designed and/or synthesized) to have distinct melting temperatures ($T_m$). With distinct melting temperatures, the efficiency of target amplification for the targets can be detectably different, with a distinct signal amplitude produced at the endpoint, under the thermal conditions (e.g., annealing temperature) used to promote amplification. The primers for one of the targets, in this case target A, may be selected to have a higher melting temperature than the primers for the other target(s), in this case target B, when bound to the template/amplicon for the respective targets. The primers may have different lengths and/or distinct base contents (e.g., different percentage of A+T or G+C). For example, the primers for one of the targets may have a greater minimum length (and/or average length) than the primers for the other target(s). In the depicted embodiment, the primers for target B, $F_B$ and $R_B$, are each shorter than the primers for target A, $F_A$ and $R_B$.

The amplification efficiency for a given pair of primers may be determined at least predominantly by the less efficient primer of the pair. Accordingly, the primers may be designed with only one of the primers for one of the targets (e.g., target B) having a lower melting temperature than both of the primers for the other target(s) (e.g., target A). For example, the forward (or reverse) primer for target B may be shorter (and/or may have a lower $T_m$) than both of the target A primers, as shown, and the reverse (or forward) primer for target B may have the same length (or may be longer) than both target A primers, with the same or even a higher melting temperature than both of the target A primers.

Any suitable algorithm may be utilized to design primers of the same or different lengths, with distinct melting temperatures. The algorithm may operate with any suitable parameters, such as length (number of nucleotides), base content, salt concentration and/or ionic strength of the reaction mixture, pH, and/or the like. An exemplary melting temperature algorithm that may be used is shown in the following equation:

$$T_m = (wA + xT)*2 + (yG + zC)*4 \tag{6}$$

where wA, xT, yG, and zC are the number of bases A, T, G, and C, respectively, in the primer sequence. Another exemplary melting temperature algorithm that may be used is shown in the following equation:

$$T_m = 64.9 + 41*(yG + zC - 16.4)/(wA + xT + yG + zC) \tag{7}$$

where wA, xT, yG, and zC are as defined above. Still another exemplary melting temperature algorithm that takes into account the salt concentration of the reaction mixture is shown in the following equation:

$$T_m = 100.5 + \left(41 * \frac{yG + zC}{(wA + xT + yG + zC)}\right) - \left(\frac{820}{wA + xT + yG + zC}\right) + 16.6 * \log_{10}([Na^+]) \tag{8}$$

Figure 9:
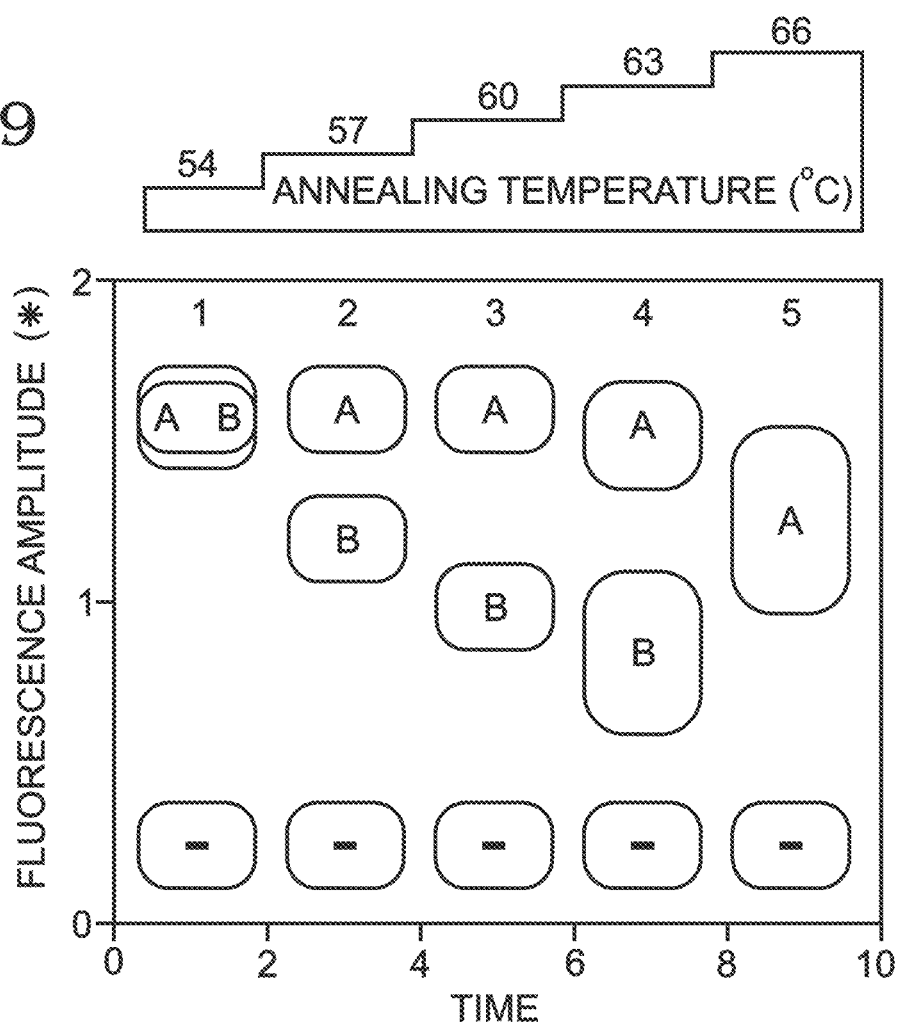
FIG. 9 is a graph of exemplary data including fluorescence amplitude that may be collected from separate sets of partitions (lanes 1-5) formed with the same reaction mixture according to FIG. 8, with amplification of the targets being performed at a single annealing temperature in a well containing both the primer set optimized to this one annealing temperature and one primer set non-optimized at this annealing temperature yet still able to amplify albeit at a lesser efficiency, and with each band of partitions identified in the graph according to target content, in accordance with aspects of the present disclosure.

FIG. 9 shows a graph of exemplary data including fluorescence amplitude (in arbitrary units) that may be collected from separate sets of partitions (lanes 1-5) detected serially with a detector as a function of time (in arbitrary units). A time gap separates each set of partitions. The partitions may be formed with the same reaction mixture according to FIG. 8. Each band or cluster of partitions is identified in the graph according to target content. Amplification of each set of partitions may performed by thermocycling at a different annealing temperature for the set, as indicated, which may facilitate identification of a suitable annealing temperature that gives an acceptable or optimal resolution of the bands representing the presence of one target (A or B) or the absence of both targets (−).

The various annealing temperatures indicated may produce substantive differences in the resolution and sharpness of the various bands of each set. Lane 1 shows little or no resolution of target B-positive partitions from target A-positive partitions. Lanes 2 and 3 show that increasing the annealing temperature may resolve target A-positive partitions from target B-positive partitions, with an annealing temperature of 60 degrees giving better separation. Lane 4 shows that a further increase in the annealing temperature may cause one or both of the target-positive bands to increase in size (e.g., smear downward) and/or shift downward toward the band of negative partitions. Lane 5 shows that a still further increase of the annealing temperature may cause amplification of target B, with its primers of lower melting temperature, to become undetectable.

II. EXAMPLES

The following examples describe selected aspects of multiplexed digital assays with a generic reporter. These examples are intended for illustration only and should not limit the entire scope of the present disclosure.

Example 1. Exemplary Multiplex Data Collected from Droplets with a Generic Reporter This example describes exemplary data collected from droplets containing a generic reporter, and supporting the strategies of FIGS. 4-9; see FIGS. 10-12.

Figure 10:
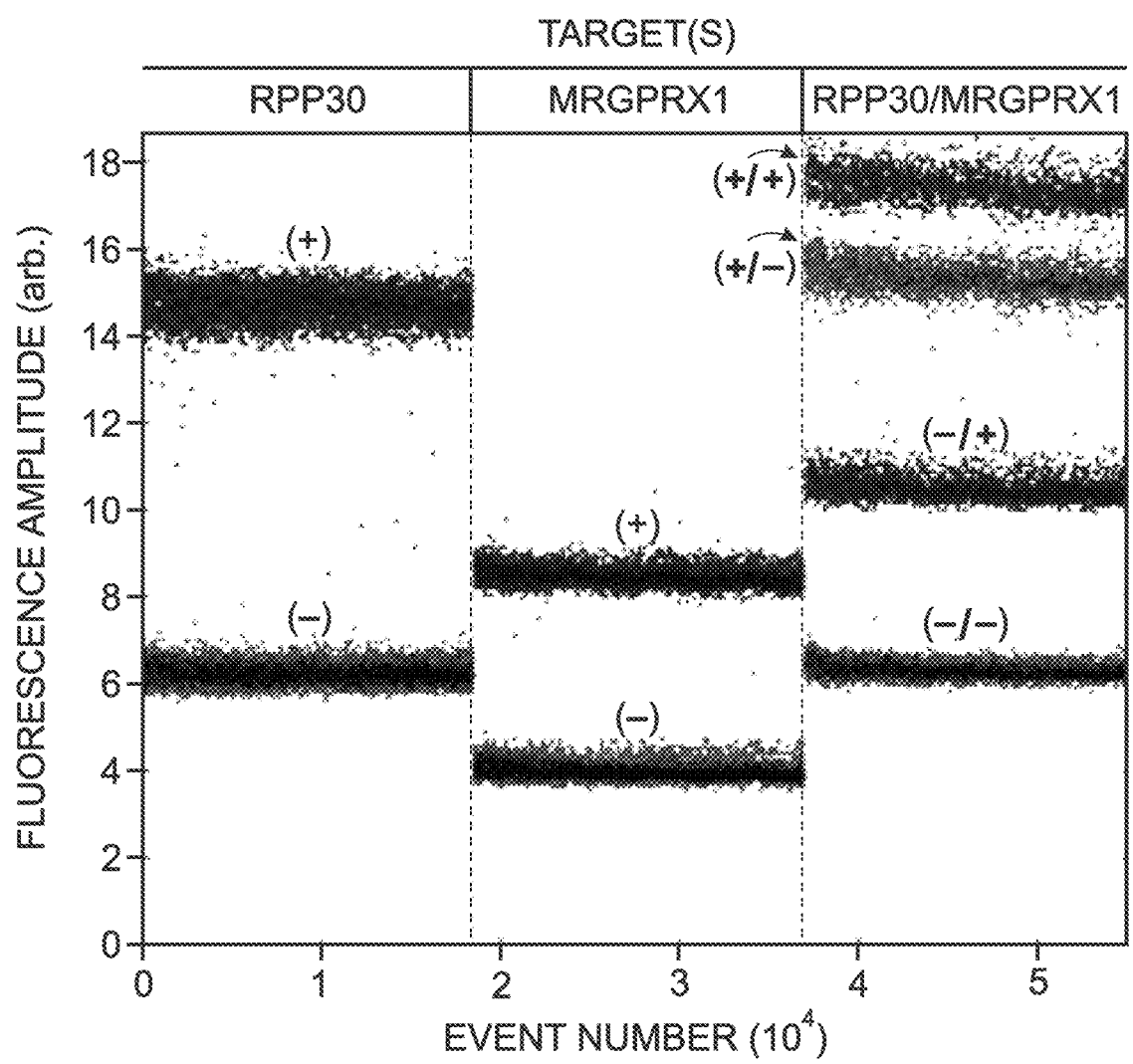
FIG. 10 is a plot of fluorescence amplitude data collected from droplets generally according to the strategy described in FIGS. 4 and 7.

FIG. 10 shows data from a multiplexed assay performed in droplets with a generic reporter (the fluorescent dye sold under the trademark EVAGREEN®), and primers for RPP30 and MRGPRX1 at different concentrations. More particularly, a RPP30 primer set was added at a final concentration of 50 nM, and a MRGPRX1 primer set was added at a final concentration of 150 nM. The RPP30/MRGPRX1 well shows three distinct amplification-positive populations of droplets containing no amplicon, MRGPRX1 amplicon only, RPP30 amplicon only, and amplicons for both RPP30 and MRGPRX1, in order from lowest to highest fluorescence amplitude. The data was generated using the strategy described in FIGS. 4 and 7.

Figure 11:
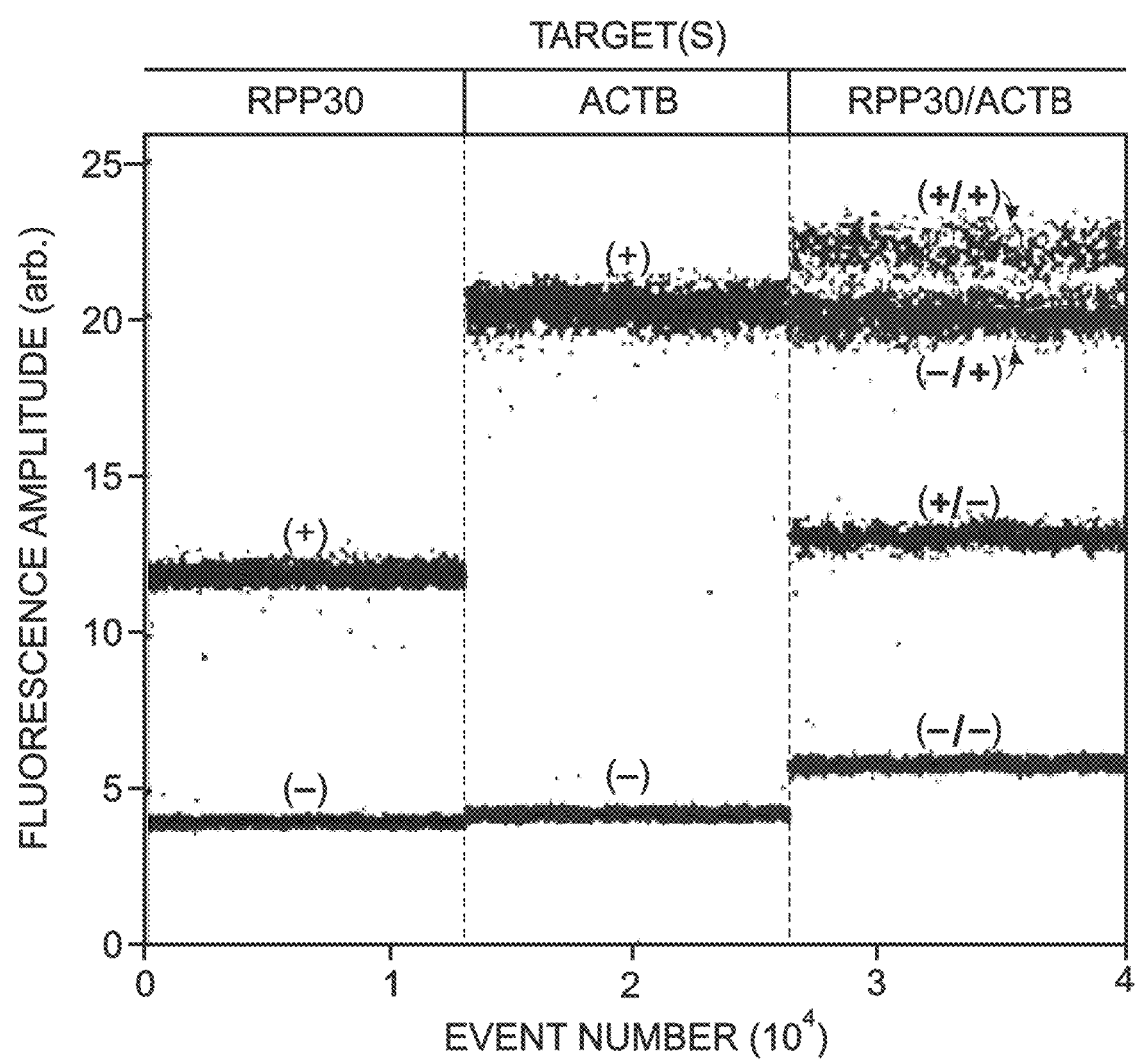
FIG. 11 is a plot of fluorescence amplitude data collected from droplets generally according to the strategy described in FIGS. 5 and 6.

FIG. 11 shows data from a multiplexed assay performed in droplets with a generic reporter (the fluorescent dye sold under the trademark EVAGREEN®), and primers for RPP30 and ACTB that produce amplicons of different length. More particularly, the primers for RPP30 generate a 62 base pair amplicon, and the primers for ACTB generate a 147 base pair amplicon. The RPP30/ACTB well shows three distinct amplification-positive populations of droplets containing neither amplicon, RPP30 amplicon only, ACTB amplicon only, and amplicons for both RPP30 and ACTB, in order from lowest to highest fluorescence amplitude. The data was generated using the strategy described in FIGS. 5 and 6.

Figure 12:
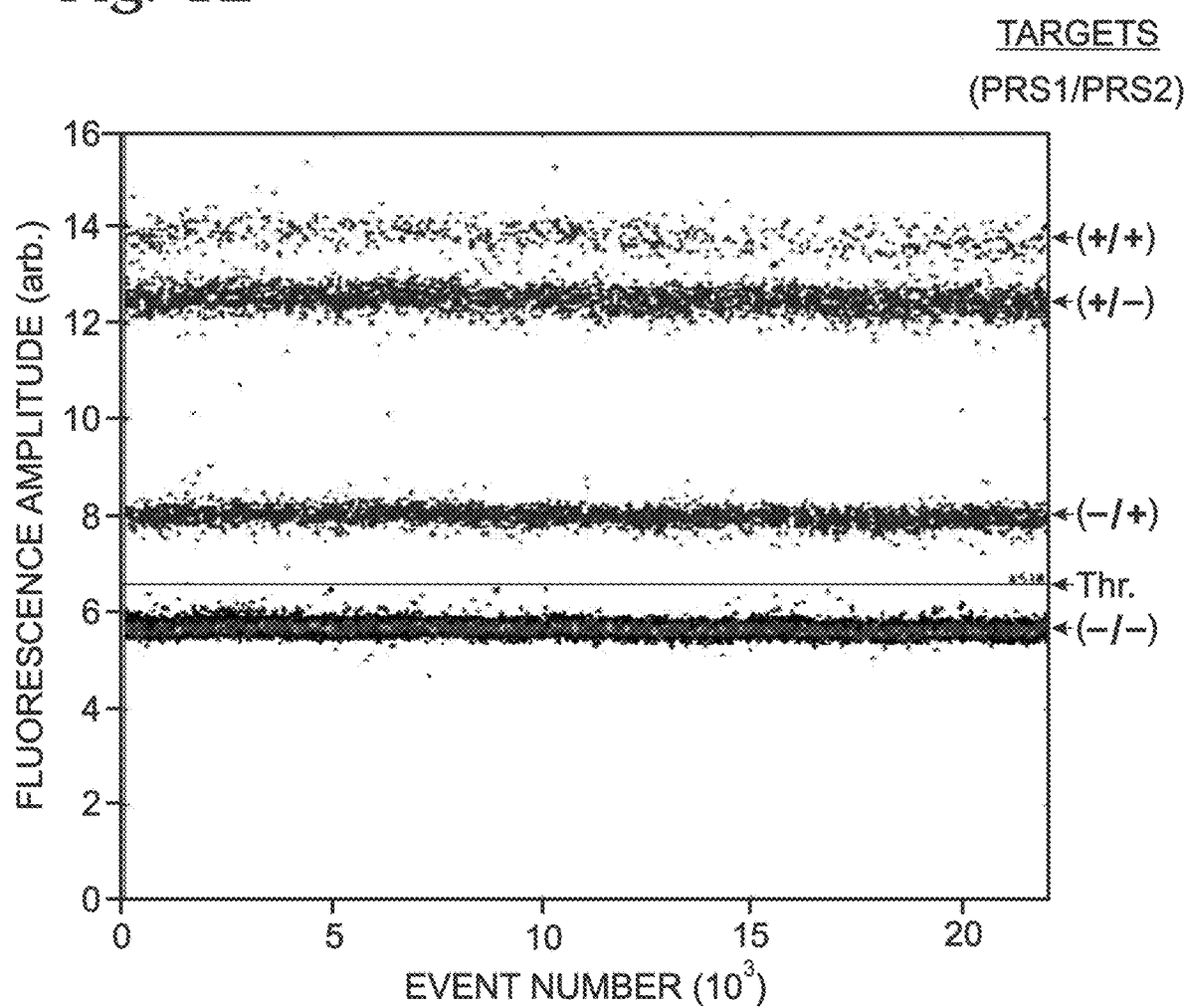
FIG. 12 is a plot of fluorescence amplitude data collected from droplets generally according to the strategy described in FIGS. 8 and 9.
Figure 13A:
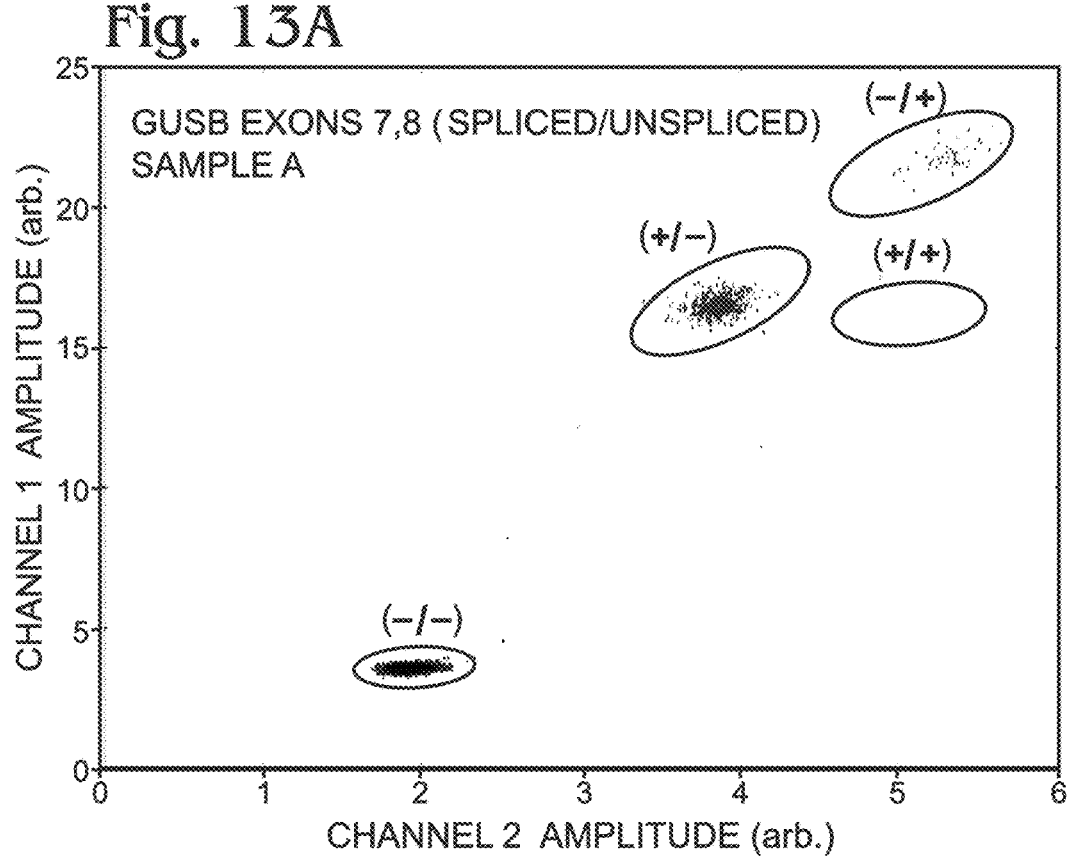
FIGS. 13A to 13D are scatter plots of amplification data collected in a pair of wavelength regimes (channels 1 and 2) from droplets containing different dilutions of a sample (A to D, respectively) after amplification of a spliced form and an unspliced form of a beta-glucuronidase (GUSB) target in the droplets, with each droplet containing the same generic reporter (the fluorescent dye sold under the trademark EVAGREEN®), and with each cluster of droplets identified according to target content (spliced/unspliced, respectively), in accordance with aspects of the present disclosure.
Figure 13B:
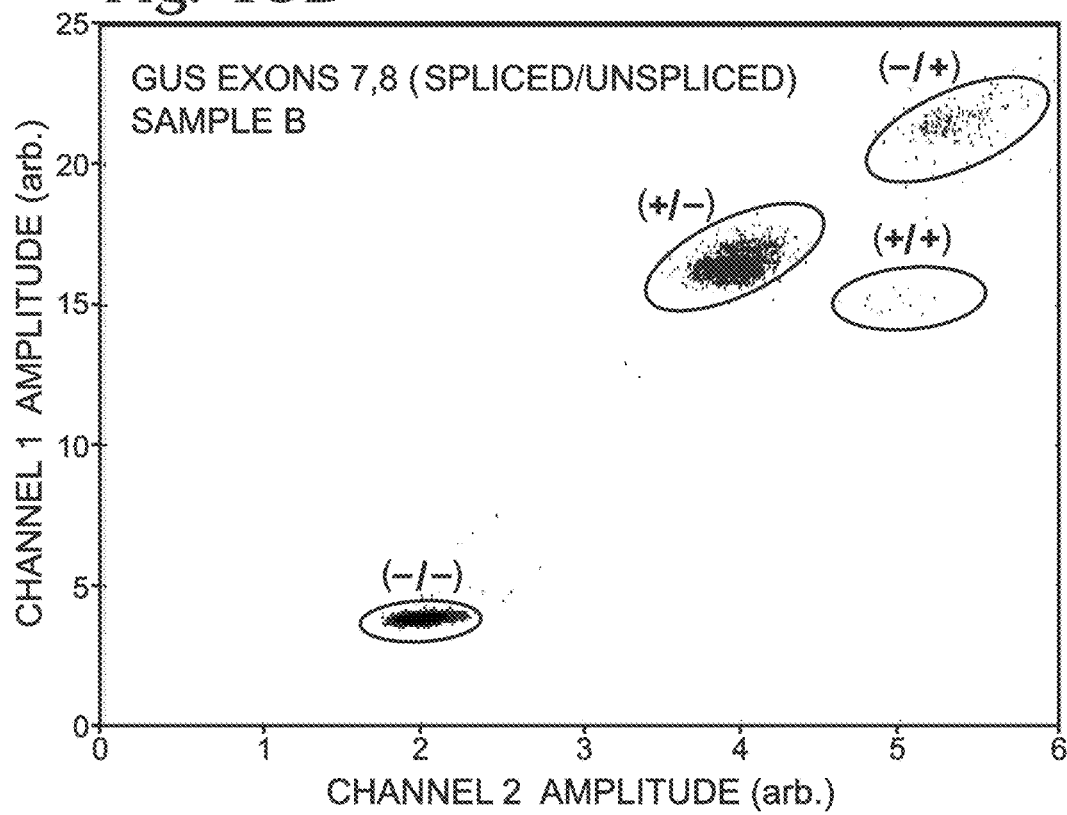
Figure 13C:
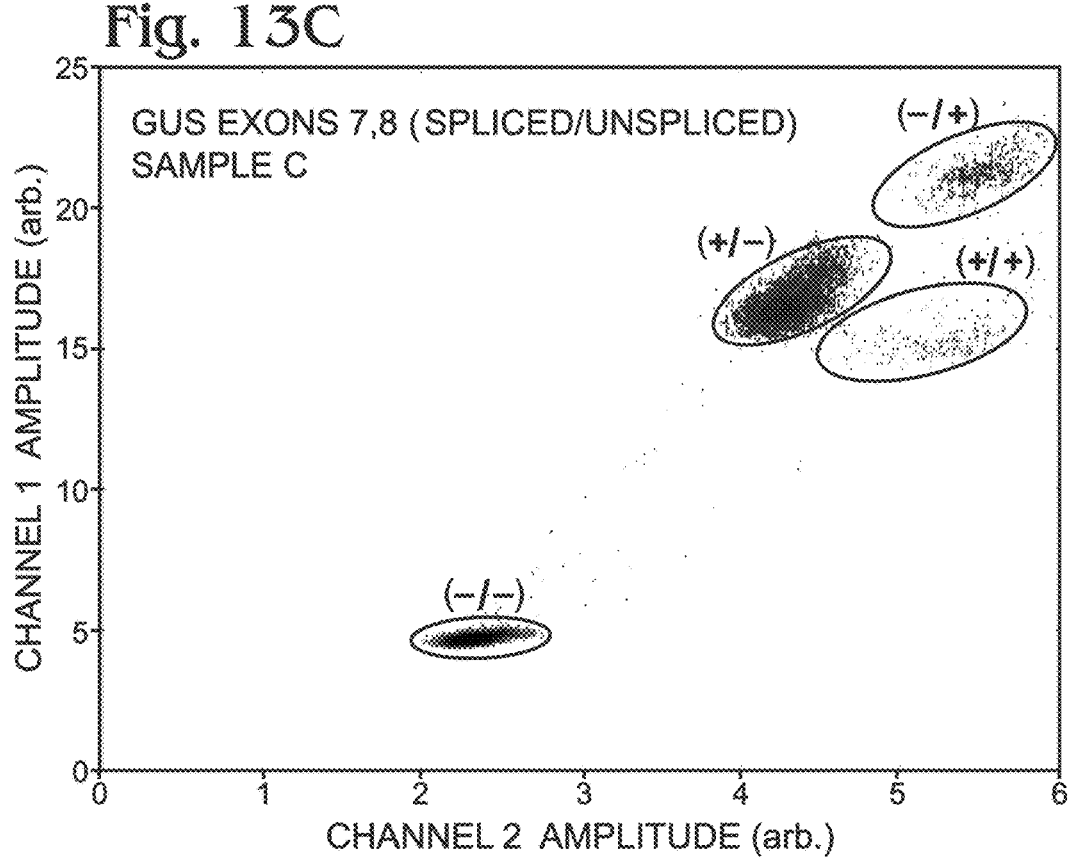
Figure 13D:
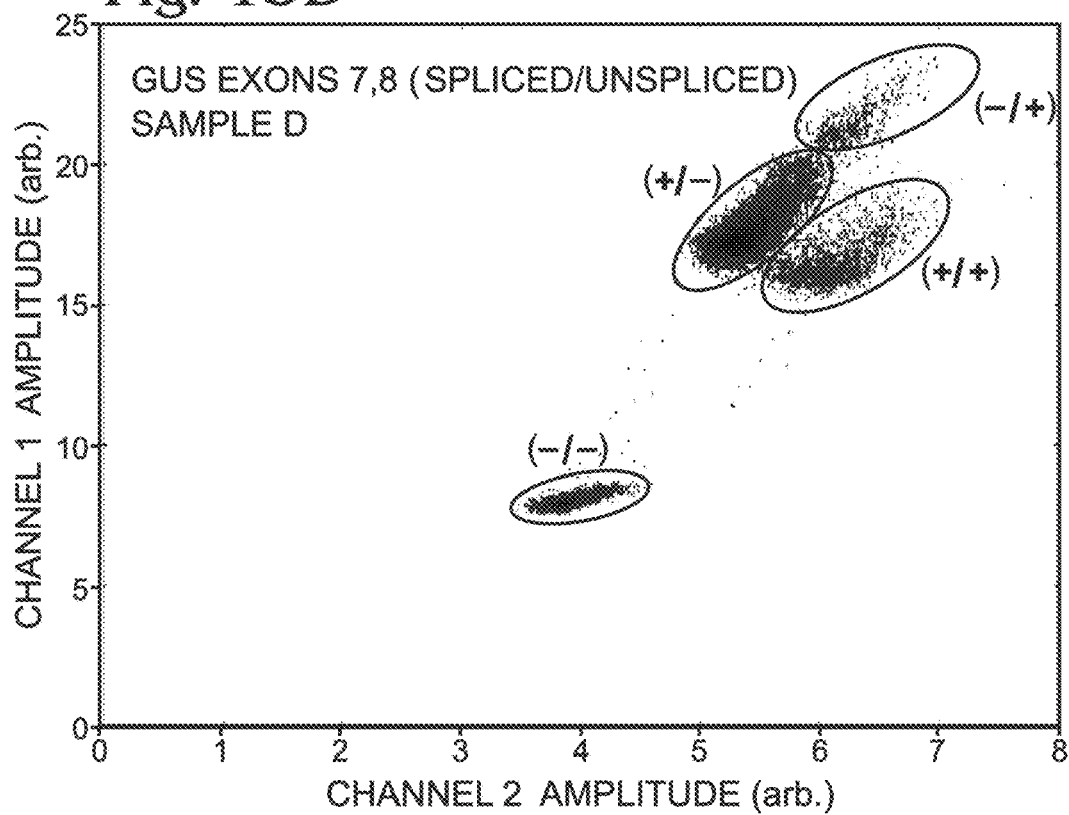
Figure 14:
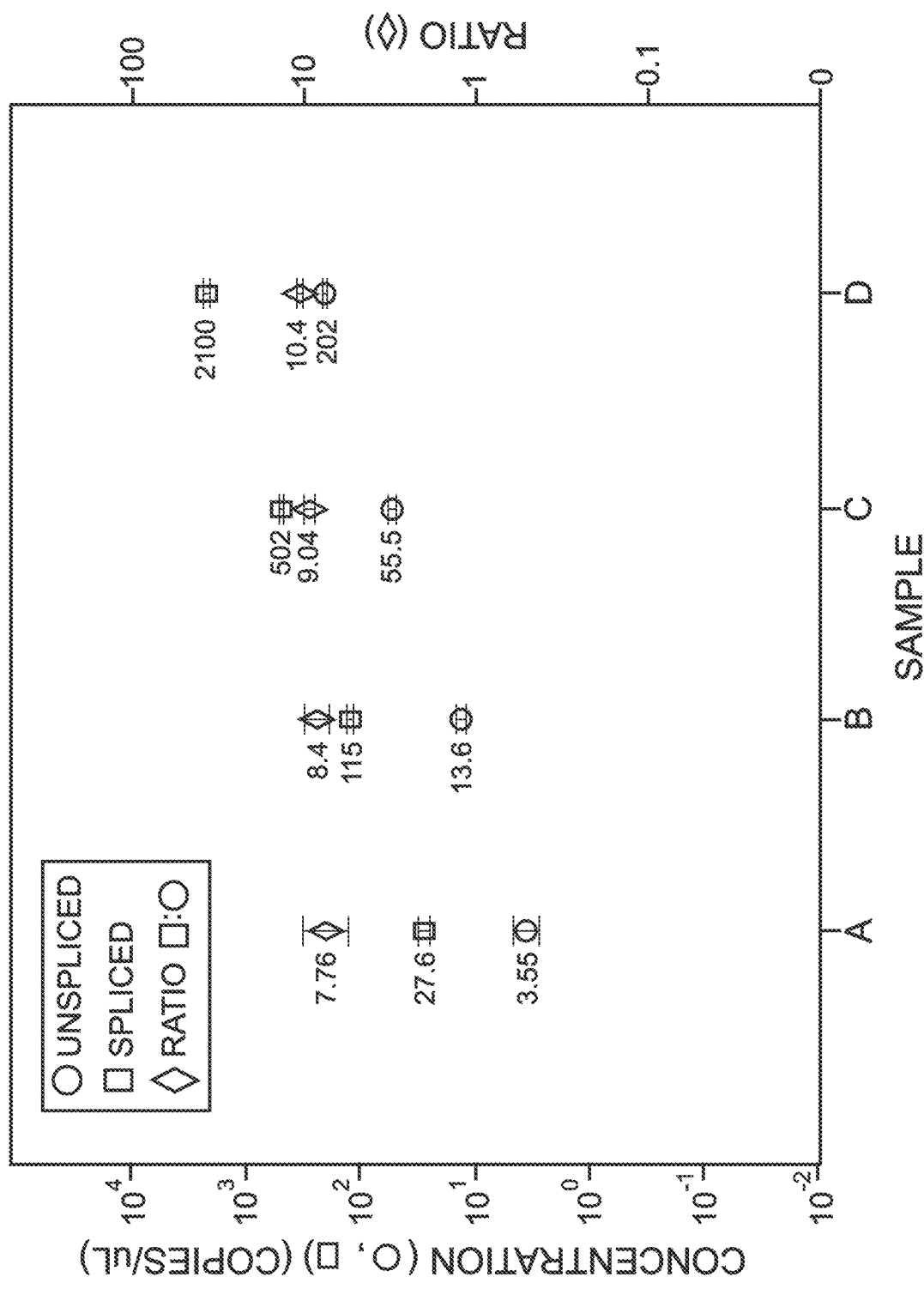
FIG. 14 is a graph of the concentrations of the spliced and unspliced forms of the GUSB targets calculated from the data of FIGS. 13A to 13D (samples A to D), and the ratio (spliced:unspliced) of the calculated target concentrations for each sample, in accordance with aspects of the present disclosure.

FIG. 12 shows data from a multiplexed assay performed in droplets with a generic reporter (the fluorescent dye sold under the trademark EVAGREEN®), and primers for PRS1 and PRS2 that produce amplicons of the same length with different efficiencies as tested here. An annealing temperature of 63° C. was used. PRS1 is amplified with a primer set having an annealing temperature optimized to 63° C. PRS2 is amplified with a primer set having an annealing temperature optimized to 59° C. Three positive populations of droplets are shown. PRS2 amplified with a lower efficiency due to the use of a non-optimized annealing temperature. PRS1 amplified with an optimized PCR efficiency. Double-positive (PRS1/PRS2) droplets have both targets amplified. The data was generated using the strategy described in FIGS. 8 and 9.

Example 2. Exemplary Multiplexing with Different Primer Concentrations

This example describes further aspects of multiplexed digital assays with a generic reporter.

A multiplexed assay for two or more targets may be performed in droplets with the fluorescent dye sold under the trademark EVAGREEN® as the reporter for assay of each target. Amplified targets (amplicons) from a duplex reaction with primer pairs at the same concentration may be detected at overlapping fluorescence amplitudes, to produce a mixed population/cluster of target-positive droplets, making it difficult to distinguish the subset of partitions positive for each particular target. The sample duplex reaction performed with the primer pairs for the two targets at different concentrations may produce two distinct and separate populations of amplified targets in droplets, enabling identification and quantification of each target. Amplitudes of the two target-positive populations in the duplex reaction may match those in the respective singleplex reactions, suggesting the majority of droplets in each population contain the amplicon for the same target.

Separate amplicon populations persist in duplex reactions containing a two-fold difference in primer concentrations for the two targets and a ten-fold range of different concentrations of templates corresponding to the two targets.

The level of multiplexing may be increased (e.g., to three targets). Singleplex and triplex PCR reactions may be performed with a fragmented form of a larger DNA template. The DNA template initially may contain all three targets linked to one another, but may be digested before droplet formation, to separate the targets on their own respective template fragments, which allows each droplet to contain only one target in the triplex reaction. The targets may be disposed in droplets at partial occupancy and then amplified. The amplified targets may be distinguished based on the different fluorescence intensity of the fluorescent dye sold under the trademark EVAGREEN® complexed with each amplicon. Increasing amounts of amplicon may produce a brighter signal because more amplicon DNA is available for binding by the fluorescent dye sold under the trademark EVAGREEN®. Adjusting primer concentrations to affect amplicon yield and fluorescence output can create separation of target populations. A higher level of multiplexing can be achieved using this method to produce a separate fluorescence band or cluster for each target.

Example 3. Analysis of Beta-glucuronidase (GUSB) for Alternative Splicing

This example describes exemplary data obtained with the digital assay system of Section I to distinguish long and short forms of GUSB RNA produced by alternative splicing; see FIGS. 13A-D and 14.

FIGS. 13A to 13D show scatter plots of amplification data (photoluminescence intensity) collected in a pair of wavelength regimes (channel 1 (e.g., a FAM dye channel) and channel 2 (e.g., a VIC dye channel)) from droplets. The droplets contained different dilutions of a cDNA sample (A to D, in FIGS. 13A to 13D, respectively). Amplification was performed with a forward primer and a reverse primer that respectively bind to exon 7 and exon 8 of GUSB. Alternative splicing of GUSB generates a shorter spliced form and a longer unspliced form of the exon 7/8 region of GUSB RNA/cDNA. Amplification of each form was detected by photoluminescence from the fluorescent dye sold under the trademark EVAGREEN® dye contained by the droplets. Photoluminescence of the dye is detectable in both optical channels.

Each cluster of droplets in each plot is identified according to target content (spliced/unspliced, respectively). Droplets negative for both targets (short and long) are identified as (−/−); droplets positive only for the shorter form are identified as (+/−); droplets positive only for the longer form are identified as (−/+); and droplets positive for both the short form and the long form are identified as (+/+). The double positive (+/+) droplets have an amplitude in channel 1 most similar to the short form-positive droplets, but have an amplitude in channel 2 most similar to the long form-positive droplets. In other words, droplets containing a copy of the short target and the long target are off-axis, because they do not fall on the roughly diagonal line connecting the other droplet clusters. Plotting the data from two optical channels allows the double-positive cluster to be distinguished from each single-positive cluster. All four distinct populations are distinguishable. In other cases, the four populations may be distinguishable using data obtained with only a single optical channel. In some embodiments, at least two of the populations may overlap, but concentrations still may be calculated as described in U.S. patent application Ser. No. 14/171,754, filed Feb. 3, 2014, which is incorporated herein by reference.

Example 4. Analysis of CAMTA1, TPM3, and ABLIM1 for Alternative Splicing

This example describes exemplary data obtained with the digital assay system of Section I to distinguish long and short forms of calmodulin binding transcription activator 1 (CAMTA1), tropomyosin 3 (TPM3), and actin binding LIM protein 1 (ABLIM1) RNA produced by alternative splicing; see FIGS. 15-19.

Forward and reverse primers were selected to opposingly flank a region of alternative splicing for each gene. The primers were predicted to produce amplicons of 57 bp and 88 bp for CAMTA1, 113 bp and 218 bp for ABLIM1, and 88 bp, 167 bp, and 1415 bp for TPM3. The longest amplicon for TPM3 (1415 bp) was not detectable in the assays. Accordingly, for each gene, two targets, a short target and a long target, are amplified and detected.

Figure 15:
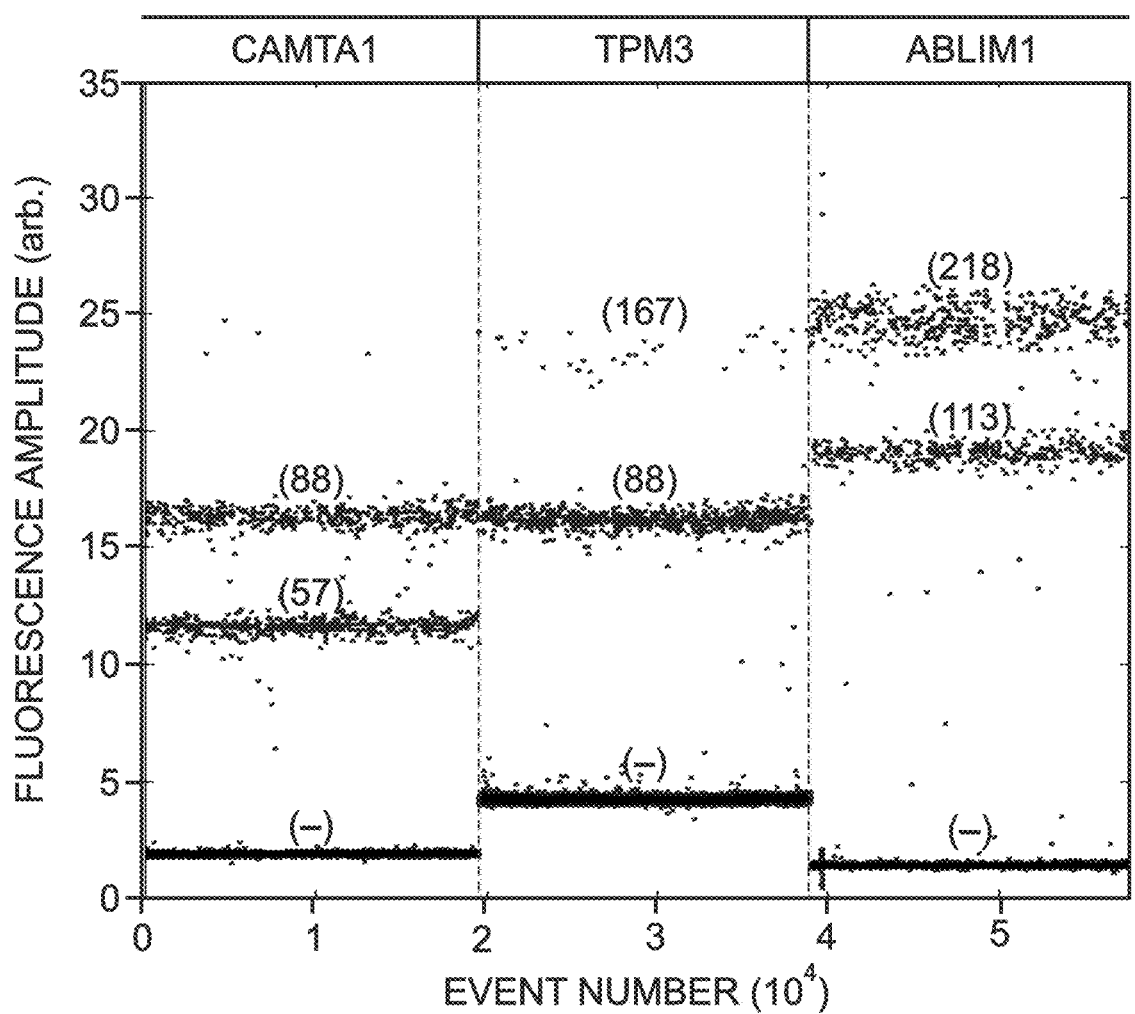
FIG. 15 is a graph of amplification data collected from three different target gene (cDNA) assays performed in droplets with a generic reporter, with each target gene (cDNA) assay detecting different spliced forms of cDNA from a target gene (CAMTA1, TPM3, or ABLIM1), in accordance with aspects of the present disclosure.

FIG. 15 shows a graph of amplification data (fluorescence amplitude) collected from droplets serially, with detection of each droplet being a numbered event in a sequence of events. The droplets each contain a generic reporter and are grouped in three sets according to the targets amplified (CAMTA1, TPM3, and ABLIM1). Each cluster or band of droplets is identified as being negative for both targets (−) or as containing a target of the size indicated in parentheses. Droplets positive for the short target and droplets positive for the long target of each gene are well resolved from each other. Double-positive droplets are not visible in FIG. 15, but, if present, may or may not have an amplitude that is higher than the two types of single-positive droplets.

Figure 16:
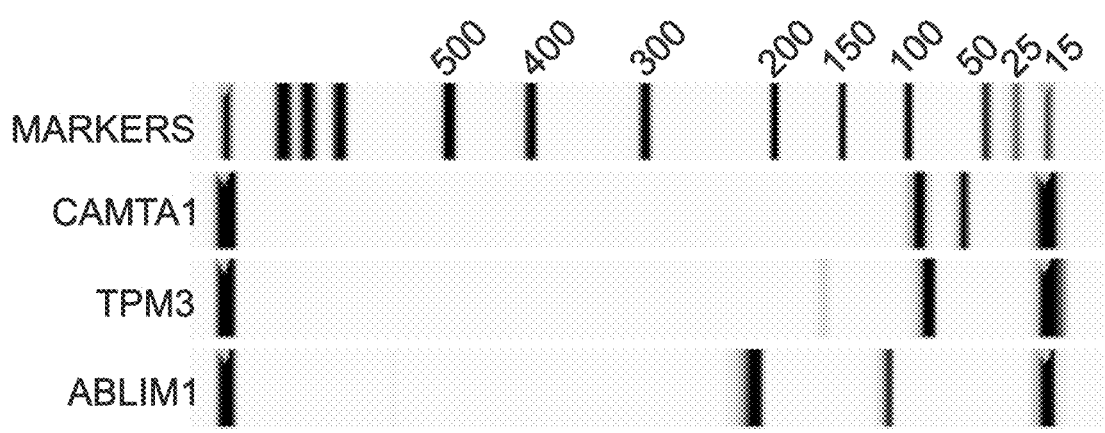
FIG. 16 is a plot of amplification data obtained by capillary electrophoresis of amplicons generated in droplets from the target gene assays of FIG. 15, in accordance with aspects of the present disclosure.

FIG. 16 shows a plot of amplification data obtained by capillary electrophoresis of amplicons generated in droplets from the target gene assays of FIG. 15. DNA was extracted from droplets of each multiplexed assay by breaking the emulsion in which the droplets are dispersed. The DNA was resolved by capillary electrophoresis and sized by comparison with a set of size markers, with the size in bp of each marker indicated. Each multiplexed assay produced a shorter amplicon and a longer amplicon of the predicted size.

Figure 17:
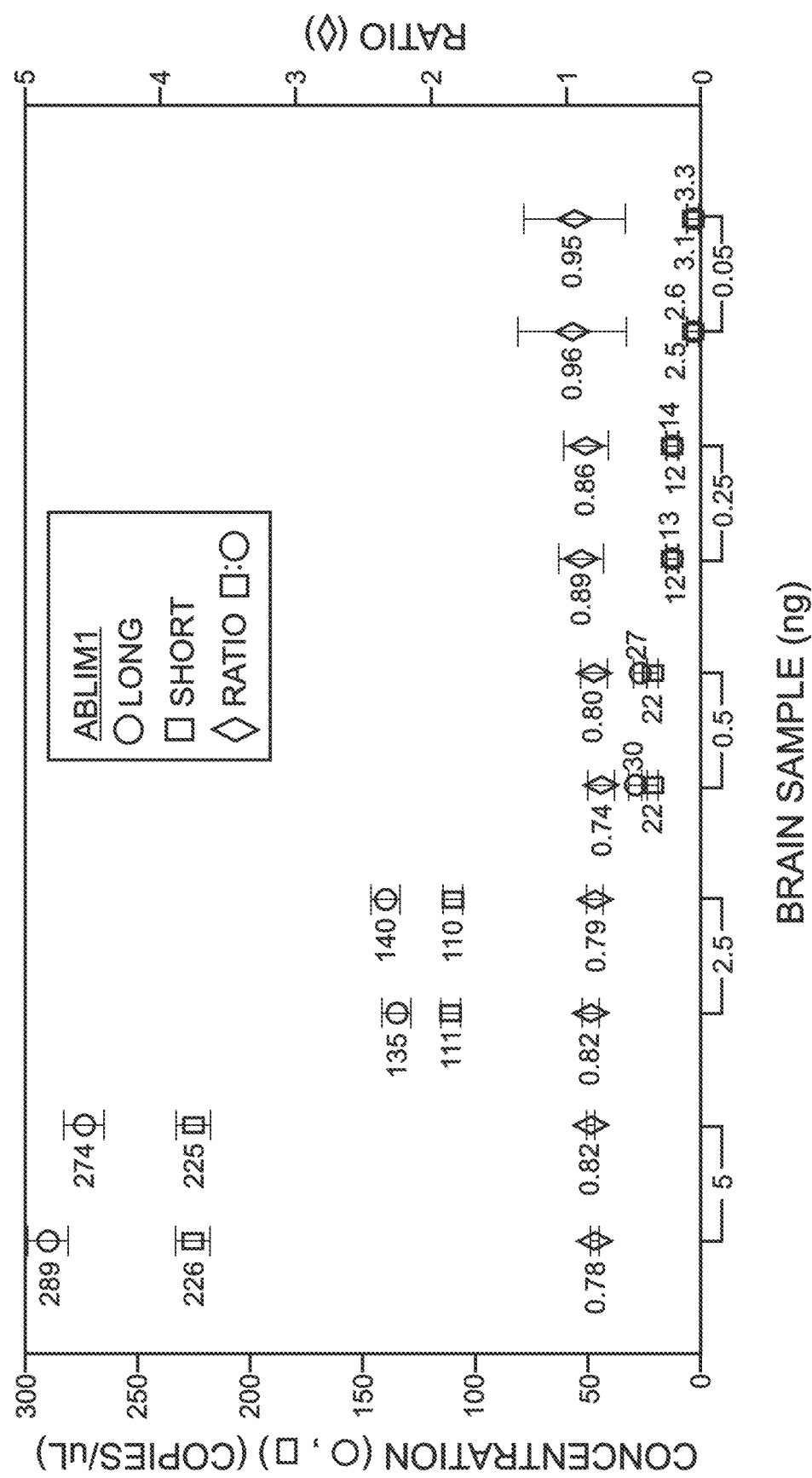
FIG. 17 is a graph of concentrations calculated for long and short, alternatively spliced forms of ABLIM1 cDNA, using amplification data from ABLIM1 assays performed as in FIG. 15 in droplets containing a generic reporter, with different concentrations of a brain RNA sample assayed, in accordance with aspects of the present disclosure.

FIG. 17 shows a graph of concentrations calculated for long (218 bp) and short (113 bp), alternatively spliced regions of ABLIM1 cDNA. The concentrations were calculated with amplification data from ABLIM1 assays performed as in FIG. 15 in droplets containing a generic reporter, with different dilutions of a brain RNA/cDNA sample assayed.

Figure 18:
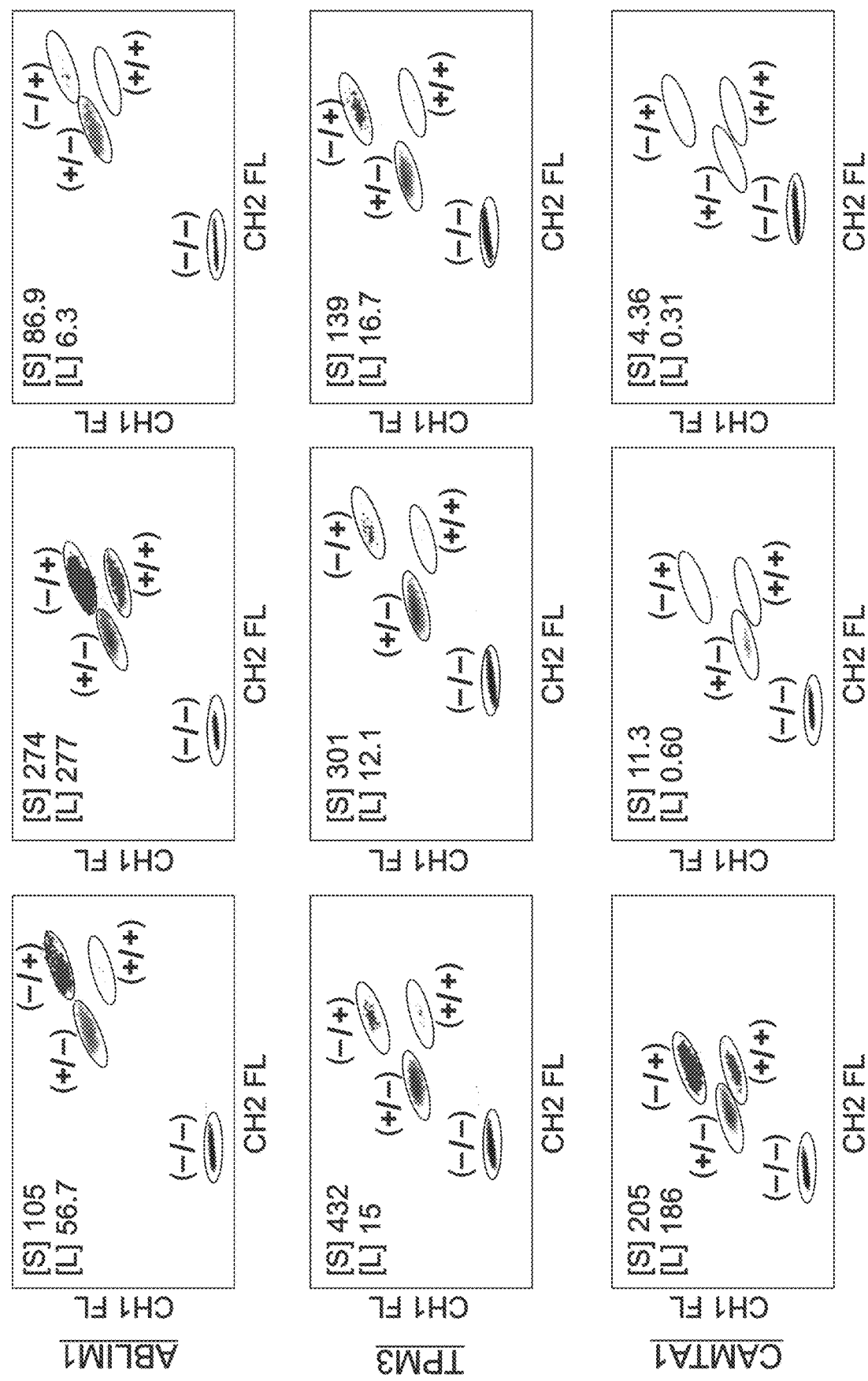
FIG. 18 is a series of scatter plots of amplification data collected from three different alternative splicing assays (ABLIM1, TPM3, and CAMTA1) performed in droplets with a generic reporter, with each different splicing assay using RNA/cDNA obtained from three different tissue sources (brain, heart, and skeletal muscle), and with each cluster of droplets identified in each plot according to target content (short form (S)/long form(L)) of alternatively spliced targets, in accordance with aspects of the present disclosure.

FIG. 18 shows a series of scatter plots of amplification data collected as fluorescence (FL) in two different optical channels (CH1 and CH2) from the three different alternative splicing assays (ABLIM1, TPM3, and CAMTA1) described for FIG. 15. The assays were performed in droplets containing a generic reporter. Each different alternative splicing assay tested RNA/cDNA obtained from three different tissue sources (brain, heart, and skeletal muscle). Each cluster of droplets is identified in each plot according to target content (short form (S)/long form(L)) of alternatively spliced targets. The concentration of the short form [S] and long form [L] calculated from the data of each plot is listed in the upper left corner of each plot.

Figure 19:
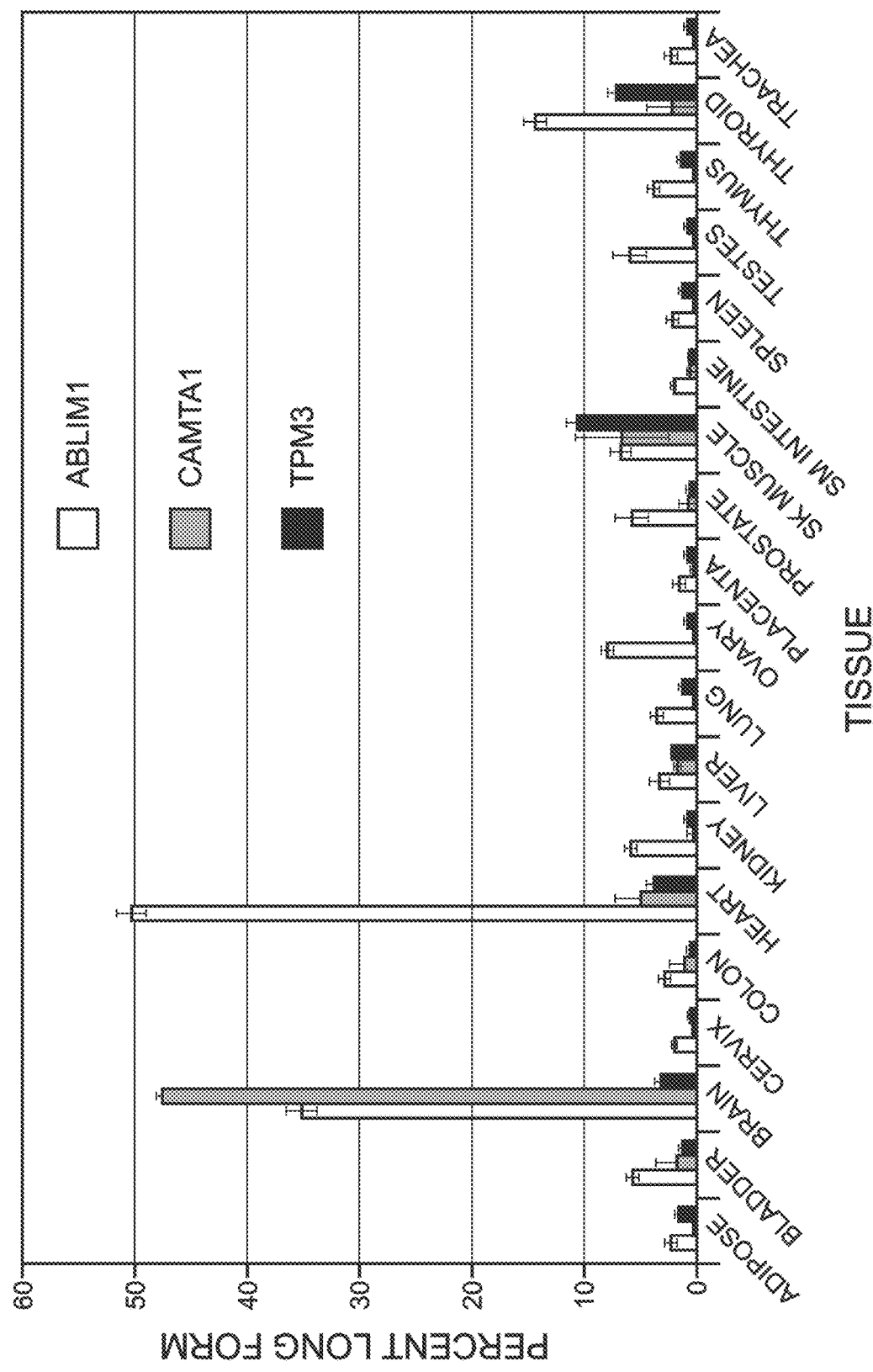
FIG. 19 is a graph of concentration data (percent long form (L)) calculated from three different alternative splicing assays (ABLIM1, CAMTA1, and TPM3) performed in droplets with a generic reporter and RNA/cDNA obtained from one of various indicated tissue sources, in accordance with aspects of the present disclosure.

FIG. 19 shows a graph of concentration data (percent long form (L)) calculated from three different alternative splicing assays (ABLIM1, TPM3, and CAMTA1) performed as described for FIG. 15. The assays were performed in droplets with a generic reporter and RNA/cDNA obtained from one of various indicated tissue sources. The percent long form was calculated as [L]/([S]+[L]) for each tissue.

Example 5. Post-amplification Thermal Conditioning for Signal Stabilization

Figure 20:
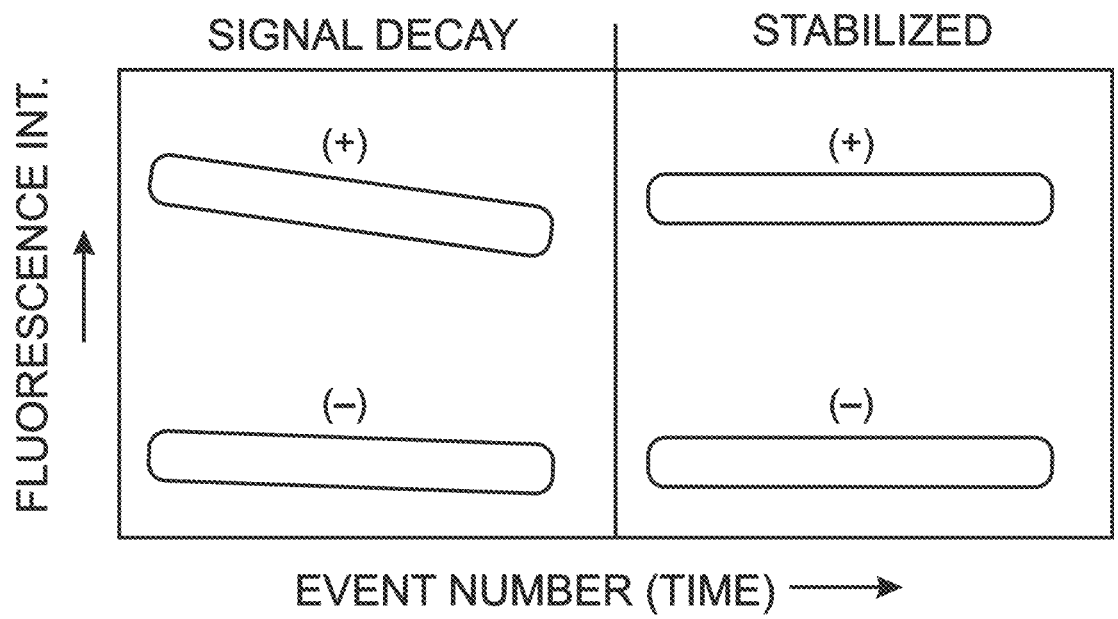
FIG. 20 is a schematic graph showing amplification data that may be obtained from partitions containing a generic reporter, with a decay in the detected signal amplitude of positive partitions occurring over time (left side), or with the signal amplitude stabilized by thermal conditioning (right side), in accordance with aspects of the present disclosure.

This example describes an exemplary signal decay that may be observed in assays performed with a generic reporter, and a thermal conditioning process that may produce signal stabilization; see FIG. 20.

FIG. 20 shows a schematic graph of amplification data that may be obtained from partitions containing a generic reporter. The partitions may be cycled thermally through multiple cycles of heating and cooling to produce denaturation and then annealing and extension. For example the partitions may be heated to a temperature of at least about 85 or 90 degrees Celsius, and then cooled to a temperature of about 55 to 75 degrees Celsius, for multiple cycles (such as at least 10, 15, or 20 cycles). Fluorescence may be measured from the partitions serially, as plotted. Target-positive (+) partitions form a band of higher signal amplitude, and target-negative (−) partitions form a band of lower signal amplitude.

The set of partitions on the left exhibits a variable signal intensity, with a marked signal decay over time, particularly for the positive partitions. This time-dependent change in signal can introduce error into the target concentration calculated, may complicate identification of target-positive populations, and may cause distinct populations to overlap, particularly in a multiplexed assay. The signal decay may be characteristic of a generic reporter in a digital assay.

The set of partitions on the right may be thermally conditioned after thermal cycling, to stabilize the signal detectable from the partitions. Thermal conditioning may include any combination of (a) cooling the partitions to a temperature of less than about 20, 10, or 5 degrees Celsius, (b) heating the partitions to a temperature of at least about 80, 85, or 90 degrees Celsius, and (c) cooling the partitions to a temperature of less than about 20, 10, or 5 degrees Celsius. Steps (a) to (c) may be performed in order. The partitions may be held at each conditioning temperature for any suitable length of time, such as at least about 10 or 30 seconds, or at least about 1, 2, or 5 minutes, among others. The partitions may be held at the final conditioning temperature indefinitely, and the signal may be stabilized indefinitely after the partitions have been thermally conditioned. In an exemplary embodiment, the partitions may be cooled at 4 degrees Celsius for 5 minutes, heated at 90 degrees Celsius for 5 minutes, cooled again at 4 degrees Celsius and then left at that temperature indefinitely until a user is ready to measure signals from the partitions.

Example 6. Distinguishing Targets by Length and Amplification Efficiency

Figure 21:
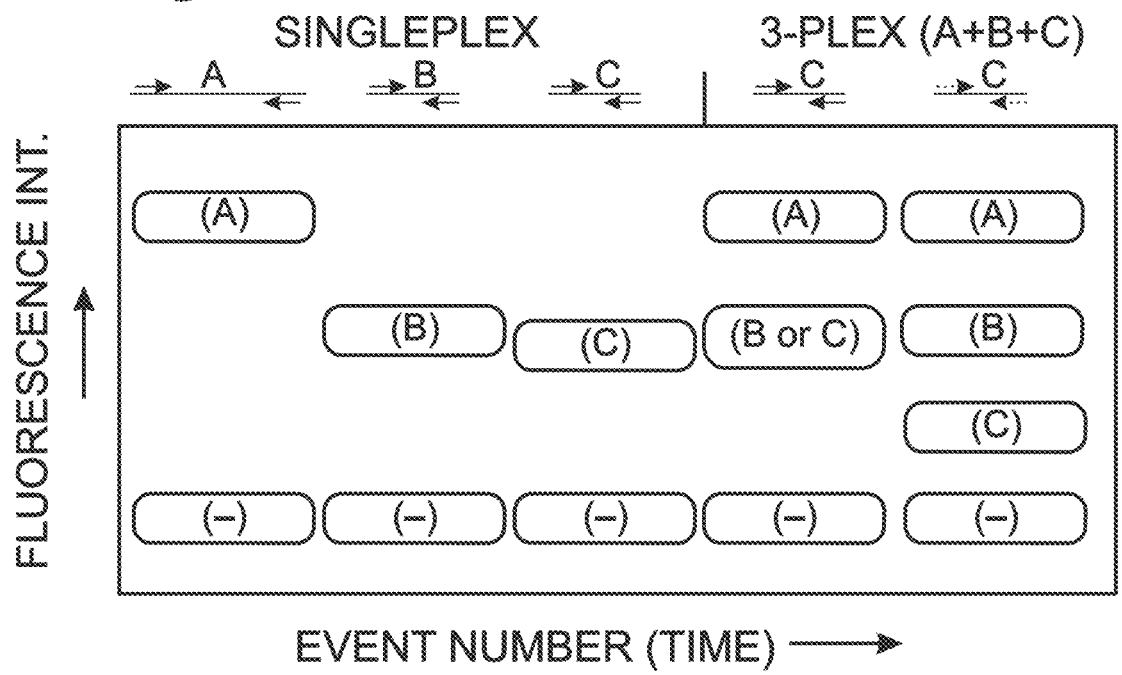
FIG. 21 is a schematic graph showing amplification data that may be obtained from singleplex assays and multiplexed assays of three different targets (A, B, and C) performed with a generic reporter, with the amplification strategy for each target shown schematically above a corresponding portion of the data, in accordance with aspects of the present disclosure.

This example describes exemplary multiplexed assays that may be performed with a generic reporter and at least three targets, with the targets distinguishable in partitions by the amplitude of photoluminescence measured from the generic reporter in partitions after target amplification; see FIG. 21.

FIG. 21 shows a schematic graph of amplification data that may be obtained from singleplex assays and multiplexed assays of three different targets (A, B, and C) performed with a generic reporter. Data for three single-target assays ("singleplex") are shown on the left, and data for multiplexed assays (3-plex, all three targets) are shown on the right.

The amplification strategy for each target is shown schematically above a corresponding portion of the data for the singleplex assays. The three targets may (or may not) be amplified with different primers from one another. The primers may (or may not) be present at the same concentration. The three targets may have the same length or may be of different length. Here, target A is longer than targets B and C, which are about the same size as each other. Due to the length difference, the signal intensity for A-positive partitions may be greater (or less) than the signal intensity for B- and C-positive partitions, as shown here. The signal intensities for the B- and C-positive partitions may be about the same, as also shown here.

Data that may be collected from amplification of the three targets in the same set of partitions, with the same primer concentrations as in the singleplex assay, is shown in the leftward 3-plex column. The A-positive partitions are resolved from the other partitions, but the B- and C-positive partitions are not resolved from each other.

Data that may be collected from amplification of the three targets in the same set of partitions, after decreasing the primer concentrations for the C target, is shown in the rightward 3-plex column. The A-, B-, and C-positive partitions are resolved from each other and from the target-negative partitions (−).

Example 7. Distinguishing Targets and Byproducts with a Generic Reporter

Figure 22:
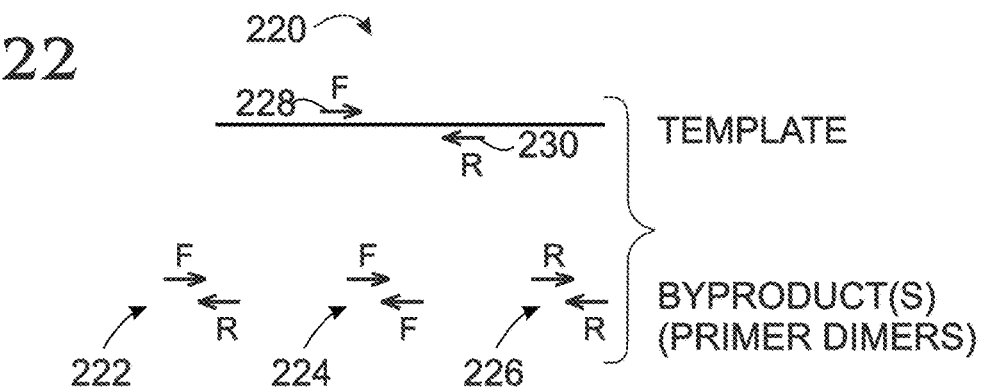
FIG. 22 is a schematic comparison of a target to be amplified from a template and various primer dimers that may be distinguished from the target in the digital assay of FIG. 1 performed with only one target and a generic reporter, in accordance with aspects of the present disclosure.
Figure 23:
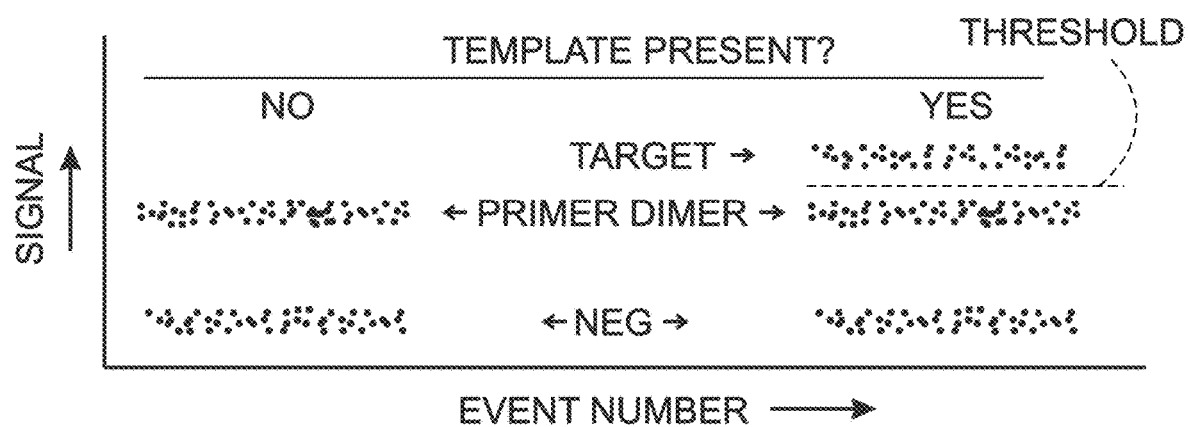
FIG. 23 is a plot of exemplary luminescence data that may be collected in a digital assay with the primers and template of FIG. 22, with at least one byproduct (primer dimer) being amplified in only a subset of the droplets the target-negative droplets, in accordance with aspects of the present disclosure.

This example describes use of the digital assay system of Section I with a generic reporter to distinguish amplification of a target from at least one amplification byproduct; see FIGS. 22 and 23.

FIG. 22 shows a template 220 containing a target and primer dimers 222-226 that may be distinguished from the target in the digital assay of FIG. 2. The target and each of the primer dimers may be amplifiable with the same pair of primers 228, 230. Accordingly, one or more of the primer dimers shown can increase background by generating false-positive droplets, particularly with a generic reporter. However, if the target has a different length and/or amplification efficiency than each byproduct that is amplified, partitions containing amplified target can be distinguished from those with amplified primer dimer based on a distinguishable signature (e.g., a different amplitude of photoluminescence detected from each partition).

FIG. 23 shows a graph plotting exemplary luminescence data that may be collected in the digital assay of FIG. 1 performed in droplets containing the target template and primers of FIG. 22. The photoluminescence intensity of droplets containing amplified target is distinguishably higher than for droplets containing amplified primer dimer (or no detectable amplification (NEG)). Here, primer dimer amplification occurs stochastically, that is, in only a subset of the droplets in the negative control. In other cases, primer dimer amplification may occur in substantially every droplet that lacks at least one copy of the target. In any event, amplification of the target may outcompete and/or suppress amplification of primer dimer in target-positive droplets. A level of the target may be calculated from the number of droplets that are amplification positive (or that are amplification negative) for the target. Droplets positive for an amplification byproduct can be classified as amplification negative for the target and can contribute to the total count (target positive plus target negative) used for calculating the target level.

Measurement of the intensity level of primer-dimer positive droplets can be used to set a suitable intensity threshold for droplets that are positive for a desired target. In particular, the signal amplitude produced by primer-dimer positive droplets in a negative control assay can be used to select a threshold above that amplitude, as shown on the right in FIG. 23, to identify the primer-dimer positive droplets as negative for the target.

Example 8. Selected Embodiments I

This example presents selected embodiments of the present disclosure as a series of numbered paragraphs.

1. A method of performing a multiplexed digital assay, the method comprising: (A) selecting primers and concentrations thereof for amplification of first and second targets to generate corresponding first and second amplicons that are distinguishable with a generic reporter; (B) forming partitions each containing the generic reporter and the primers at the selected concentrations, wherein a template for each target is present at partial occupancy in the partitions; (C) amplifying the first target and the second target in the partitions; (D) detecting light emitted by the generic reporter from individual partitions; and (E) determining a level of each target based on the light detected.

2. The method of paragraph 1, wherein the generic reporter includes an intercalating dye.

3. The method of paragraph 1 or 2, wherein the step of selecting includes a step of selecting a first pair of primers for amplification of the first target and a second pair of primers for amplification of the second target.

4. The method of paragraph 3, wherein each of the first pair of primers and the second pair of primers includes a same primer that is a member of both pairs and a different primer that is a member of only one of the pairs.

5. The method of paragraph 3, wherein no primer of the first pair is a member of the second pair.

6. The method of paragraph 3, wherein the first pair and the second pair of primers are selected such that the first amplicon is at least 20% longer than the second amplicon.

7. The method of any of paragraphs 1 to 6, further comprising a step of testing different concentrations of at least one of the primers by detecting an intensity of light emitted by the generic reporter after amplification of at least one of the targets with the different concentrations in different sets of partitions, wherein the step of selecting is based on the step of testing.

8. The method of paragraph 7, wherein the step of testing includes a step of varying a concentration of a primer for the first target in different sets of partitions while a concentration of a primer for the second target in the partitions is held constant.

9. The method of paragraph 8, wherein the step of testing includes a step of varying a concentration of a pair of primers for the first target while a concentration of a pair of primers for the second target in the partitions is held constant.

10. The method of paragraph 1, further comprising a step of testing different amplicon lengths for the first amplicon by detecting light emitted by the generic reporter after amplification of different forms of the first target with different pairs of first target primers in different sets of partitions, wherein the step of selecting is based on the step of testing.

11. The method of paragraph 10, wherein the step of testing includes amplification of the second amplicon in the different sets of partitions.

12. The method of paragraph 11, wherein a length of the second amplicon is constant in the different sets of partitions.

13. The method of any preceding paragraph, further comprising a step of testing different concentrations of the generic reporter in different sets of partitions by detecting light emitted by the generic reporter after amplification of at least one of the targets with the different concentrations in different sets of partitions, wherein the step of selecting is based on step of testing.

14. The method of any preceding paragraph, wherein the step of selecting the primers includes a step of selecting one or more primers according to an expected or assumed relationship between amplicon length in a partition and signal amplitude measured from the generic reporter for such partition.

15. The method of any preceding paragraph, wherein the step of selecting primers includes a step of selecting a first concentration for one or more primers that amplify the first target and a second concentration for one or more primers that amplify the second target, and wherein the first concentration is different from the second concentration.

16. The method of paragraph 15, wherein the first concentration is at least about 50% greater than the second concentration.

17. The method of paragraph 16, wherein the first concentration is at least about twice the second concentration.

18. The method of any preceding paragraph, wherein at least one of the primers for amplification of the second target has a lower melting temperature then each of the primers for amplification of the first target.

19. The method of paragraph 18, wherein each of the primers for the first target has a higher melting temperature than each of the primers for the second target.

20. The method of any preceding paragraph, wherein at least one of the primers for the second target is shorter than each of the primers for the first target.

21. The method of paragraph 20, wherein each of the primers for the second target is shorter than each of the primers for the first target.

22. The method of paragraph 18, further comprising a step of designing at least one of the primers based on a melting temperature algorithm.

23. The method of paragraph 22, wherein the step of designing at least one of the primers includes a step of designing each of the primers based on a melting temperature algorithm.

24. The method of any preceding paragraph, further comprising a step of testing different annealing temperatures for the step of amplifying with distinct sets of partitions containing a same reaction mixture.

25. The method of paragraph 24, further comprising a step of selecting an annealing temperature based on the step of testing, wherein the step of determining a level of each target is performed based on the step of amplifying performed at the annealing temperature selected.

Example 9. Selected Embodiments 11

This example presents selected embodiments of the present disclosure as a series of numbered paragraphs.

1. A method of performing a multiplexed digital assay, the method comprising: (A) forming partitions each including a portion of a same mixture, the mixture containing a first target and a second target and also containing a generic reporter that is sensitive to amplification of either target, wherein only a subset of the partitions each contain at least one copy of the first target and only a different subset of the partitions each contain at least one copy of the second target; (B) amplifying the first target and the second target in the partitions; (C) collecting amplification data from the generic reporter for a plurality of the partitions, wherein amplification of the first target in a partition is distinguishable from amplification of the second target; and (D) determining a level of each target.

2. The method of paragraph 1, wherein the amplification data is collected from the plurality of partitions at about a same temperature.

3. The method of paragraph 1 or 2, wherein the step of collecting amplification data is performed after the step of amplifying has been completed.

4. The method of any of paragraphs 1 to 3, wherein primers for the second target prime more efficiently than primers for the first target during the step of amplifying.

5. The method of paragraph 4, wherein at least one of the primers for the first target is present at a lower concentration than the primers for the second target.

6. The method of paragraph 4 or 5, wherein at least one of the primers for the first target has a lower melting temperature than the primers for the second target.

7. The method of any of paragraphs 4 to 6, wherein the at least one primer for the first target is shorter than each primer for the second target.

8. The method of any of paragraphs 1 to 7, wherein amplification of the first target in a partition is not distinguishable in the data from amplification on the second target in a partition due only to a difference, in any, of a length of the targets relative to each other.

9. The method of any of paragraphs 1 to 8, wherein the step of amplifying is performed with a first pair of primers for the first target and a second pair of primers for the second target, and wherein a concentration of at least one primer of the first pair in the partitions is less than a concentration of each primer of the second pair.

10. The method of paragraph 9, wherein a concentration of each primer of the first pair in each partition is less than a concentration of each primer of the second pair.

11. The method of any of paragraphs 1 to 10, wherein the step of amplifying is performed with a first pair of primers for the first target and a second pair of primers for the second target, and wherein at least one primer of the first pair has a lower melting temperature than each primer of the second pair.

12. The method of paragraph 11, wherein each primer of the first pair has a lower melting temperature than each primer of the second pair.

13. The method of paragraph 11 or 12, wherein at least one primer of the first pair is shorter than each primer of the second pair.

14. The method of paragraph 13, wherein each primer of the first pair is shorter than each primer of the second pair.

15. The method of any of paragraphs 1 to 14, wherein the step of amplifying is performed with a plurality of thermal cycles and a first pair of primers for generating a first amplicon corresponding to the first target and a second pair of primers for generating a second amplicon corresponding to the second target, and wherein an annealing temperature of each thermal cycle permits more efficient binding of the second pair of primers than the first pair of primers.

16. The method of any of paragraphs 1 to 15, wherein the step of amplifying includes a step of amplifying the first target to form a first amplicon and the second target to form a second amplicon, and wherein the first amplicon has a different length than the second amplicon.

17. The method of paragraph 16, wherein the step of amplifying includes a step of amplifying the first target and the second target with a same pair of primers.

18. The method of any of paragraphs 1 to 17, wherein the step of collecting amplification data includes a step of collecting photoluminescence data from the generic reporter.

19. The method of any of paragraphs 1 to 18, wherein the step of amplifying is performed with a first pair of primers for the first target and a second pair of primers for the second target, wherein (a) a concentration of at least one primer of the first pair in the partitions is less than a concentration of each primer of the second pair, (b) at least one primer of the first pair is configured to have a lower melting temperature than each primer of the second pair, (c) at least one primer of the first pair is shorter than each primer of the second pair, or (d) any combination of (a) to (c), and wherein amplification of the first target results in a weaker average signal than amplification of the second target in the data.

20. A method of performing a multiplexed digital assay, the method comprising: (A) forming partitions each including a portion of a same mixture, the mixture containing a target and also containing a generic reporter that is sensitive to amplification of the target, wherein only a subset of the partitions each contain at least one copy of the target; (B) amplifying the target and at least one byproduct in the partitions; (C) collecting amplification data from the generic reporter for a plurality of the partitions, wherein amplification in a partition of the target, the byproduct, or neither the target nor the byproduct are distinguishable from one another in the data; and (D) determining a level of the target.

21. The method of paragraph 20, wherein the byproduct includes a primer dimer.

22. The method of paragraph 20 or 21, wherein detectable amplification of the byproduct occurs stochastically in the partitions.

23. The method of any of paragraphs 20 to 22, wherein amplification of the target in a partition inhibits amplification of the byproduct.

24. The method of any of paragraphs 20 to 23, further comprising a step of assigning partitions as positive or negative for the target based on at least one threshold that selectively includes partitions positive for the target and selectively excludes partitions positive for the byproduct and partitions positive for neither the target nor the byproduct.

25. The method of any of paragraphs 20 to 24, wherein partitions positive for the target have a stronger signal from the generic reporter than partitions positive for the byproduct.

26. The method of any of paragraphs 20 to 25, wherein the step of determining a level of the target includes a step of calculating a concentration based on a fraction of the plurality of partitions that are positive for the target or based on a fraction of the plurality of partitions that are negative for the target.

27. A method of performing a multiplexed digital assay, the method comprising: (A) forming partitions each including a portion of a same mixture, the mixture containing a target and a generic reporter that is sensitive to amplification of the target, wherein only a subset of the partitions each contain at least one copy of the target; (B) thermally cycling the partitions to amplify the target; (C) stabilizing signals to be detected from the thermally cycled partitions by cooling the partitions below room temperature, heating the partitions above 80 degrees Celsius, and cooling the partitions again below room temperature; (D) collecting amplification data from the generic reporter for a plurality of the partitions; and (E) determining a level of the target.

28. A method of performing a multiplexed digital assay, the method comprising: (A) selecting primers and concentrations thereof for amplification of first and second targets to generate corresponding first and second amplicons that are distinguishable with a generic reporter; (B) forming partitions each containing the generic reporter and the primers at the selected concentrations, wherein a template for each target is present at partial occupancy in the partitions; (C) amplifying the first target and the second target in the partitions; (D) detecting light emitted by the generic reporter from individual partitions; and (E) determining a level of each target based on the light detected.

29. The method of paragraph 28, wherein the generic reporter includes an intercalating dye.

30. The method of paragraph 28 or 29, wherein the step of selecting includes a step of selecting a first pair of primers for amplification of the first target and a second pair of primers for amplification of the second target.

31. The method of paragraph 30, wherein each of the first pair of primers and the second pair of primers includes a same primer that is a member of both pairs and a different primer that is a member of only one of the pairs.

32. The method of paragraph 30, wherein no primer of the first pair is a member of the second pair.

33. The method of any of paragraphs 30 to 32, wherein the first pair and the second pair of primers are selected such that the first amplicon is at least 20% longer than the second amplicon.

34. The method of paragraph 33, further comprising a step of testing different concentrations of at least one of the primers by detecting an intensity of light emitted by the generic reporter after amplification of at least one of the targets with the different concentrations in different sets of partitions, wherein the step of selecting is based on the step of testing.

35. The method of paragraph 34, wherein the step of testing includes a step of varying a concentration of a primer for the first target in different sets of partitions while a concentration of a primer for the second target in the partitions is held constant.

36. The method of paragraph 35, wherein the step of testing includes a step of varying a concentration of a pair of primers for the first target while a concentration of a pair of primers for the second target in the partitions is held constant.

37. The method of any of paragraphs 28 to 36, further comprising a step of testing different amplicon lengths for the first amplicon by detecting light emitted by the generic reporter after amplification of different forms of the first target with different pairs of first target primers in different sets of partitions, wherein the step of selecting is based on the step of testing.

38. The method of paragraph 37, wherein the step of testing includes amplification of the second amplicon in the different sets of partitions.

39. The method of paragraph 38, wherein a length of the second amplicon is constant in the different sets of partitions.

40. The method of any of paragraphs 28 to 39, further comprising a step of testing different concentrations of the generic reporter in different sets of partitions by detecting light emitted by the generic reporter after amplification of at least one of the targets with the different concentrations in different sets of partitions, wherein the step of selecting is based on step of testing.

41. The method of any of paragraphs 28 to 40, wherein the step of selecting the primers includes a step of selecting one or more primers according to an expected or assumed relationship between amplicon length in a partition and signal amplitude measured from the generic reporter for such partition.

42. The method of any of paragraphs 28 to 41, wherein the step of selecting primers includes a step of selecting a first concentration for one or more primers that amplify the first target and a second concentration for one or more primers that amplify the second target, and wherein the first concentration is different from the second concentration.

43. The method of paragraph 42, wherein the second concentration is at least about 50% greater than the first concentration.

44. The method of paragraph 42, wherein the second concentration is at least about twice the first concentration.

45. The method of any of paragraphs 28 to 44, wherein at least one of the primers for amplification of the first target has a lower melting temperature then each of the primers for amplification of the second target.

46. The method of paragraph 45, wherein each of the primers for the second target has a higher melting temperature than each of the primers for the first target.

47. The method of any of paragraphs 28 to 46, wherein at least one of the primers for the first target is shorter than each of the primers for the second target.

48. The method of paragraph 47, wherein each of the primers for the first target is shorter than each of the primers for the second target.

49. The method of any of paragraphs 28 to 48, further comprising a step of designing at least one of the primers based on a melting temperature algorithm.

50. The method of paragraph 49, wherein the step of designing at least one of the primers includes a step of designing each of the primers based on a melting temperature algorithm.

51. The method of any of paragraphs 28 to 50, further comprising a step of testing different annealing temperatures for the step of amplifying with distinct sets of partitions containing a same reaction mixture.

52. The method of paragraph 51, further comprising a step of selecting an annealing temperature based on the step of testing, wherein the step of determining a level of each target is performed based on the step of amplifying performed at the annealing temperature selected.

53. A composition for performing a multiplexed assay, comprising: (A) a plurality of droplets each containing amplification reagents sufficient for amplifying a first target and a second target and also containing a generic reporter sensitive to amplification of either target, wherein only a subset of the droplets each contain at least one copy of the first target and only a different subset of the droplets each contain at least one copy of the second target; and (B) a continuous phase surrounding each of the droplets.

54. The composition of paragraph 53, wherein the continuous phase includes an oil.

55. The composition of paragraph 53 or 54, wherein the continuous phase includes a surfactant.

56. The composition of any of paragraphs 53 to 55, wherein the amplification reagents include at least one different primer for amplification of each target.

57. The composition of paragraph 56, wherein the amplification reagents include a first pair of primers for amplification of the first target and a second pair of primers for amplification of the second target, and wherein each primer of the first pair is distinct from each primer of the second pair.

58. The composition of any of paragraphs 53 to 57, wherein amplification of the first target forms a first amplicon, wherein amplification of the second target forms a second amplicon, and wherein the first amplicon has a different length than the second amplicon.

59. The composition of any of paragraphs 53 to 58, wherein a first subset of the droplets each contain at least one copy of the first target, wherein a different second subset of the droplets each contain at least one copy of the second target, and wherein a different third subset of the droplets each contain at least one copy of the first target and at least one copy of the second target.

60. The composition of any of paragraphs 53 to 59, wherein the generic reporter binds to double-stranded nucleic acid.

61. The composition of any of paragraphs 53 to 60, wherein the generic reporter includes a photoluminescent intercalating dye.

62. The composition of any of paragraphs 53 to 61, wherein the amplification reagents include a first pair of primers for amplification of the first target and a second pair of primers for amplification of the second target, and wherein at least one primer of the first pair is present at a lower concentration relative to each primer of the second pair.

63. The composition of paragraph 62, wherein each primer of the first pair is present at a lower concentration relative to each primer of the second pair.

64. The composition of any of paragraphs 53 to 63, wherein the amplification reagents include a first pair of primers for amplification of the first target and a second pair of primers for amplification of the second target, and wherein at least one primer of the first pair has a lower melting temperature than each primer of the second pair.

65. The composition of paragraph 64, wherein each primer of the first pair has a lower melting temperature than each primer of the second pair.

66. The composition of any of paragraphs 53 to 65, wherein the amplification reagents include a first pair of primers for amplification of the first target and a second pair of primers for amplification of the second target, and wherein at least one primer of the first pair is shorter than each primer of the second pair.

67. The composition of paragraph 66, wherein each primer of the first pair is shorter than each primer of the second pair.

68. The composition of any of paragraphs 53 to 67, wherein amplification of the first target forms a first amplicon, wherein amplification of the second target forms a second amplicon, and wherein more of the generic reporter binds to a copy of the first amplicon than to a copy the second amplicon.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of performing a digital assay, the method comprising:
    forming partitions each including a portion of a same mixture, the mixture containing a target and also containing a generic reporter that is sensitive to amplification of the target, wherein only a subset of the partitions each contain at least one copy of the target;
    amplifying the target and at least one byproduct including a primer dimer to generate target and byproduct amplicons, respectively, in the partitions;
    collecting amplification data from the generic reporter for a plurality of the partitions, wherein partitions exhibiting detectable amplification of the target, partitions exhibiting detectable amplification of the byproduct, and partitions exhibiting detectable amplification of neither the target nor the byproduct are distinguishable from one another in the data based on distinct amounts of the generic reporter being bound to the target and byproduct amplicons; and
    determining a level of the target using the amplification data.

2. The method of claim 1, wherein detectable amplification of the byproduct occurs stochastically in the plurality of partitions.

3. The method of claim 1, wherein detectable amplification of the target in a partition inhibits detectable amplification of the byproduct.

4. The method of claim 1, further comprising a step of assigning partitions of the plurality as positive or negative for the target based on a threshold that selectively includes partitions exhibiting detectable amplification of the target and selectively excludes partitions exhibiting detectable amplification of the byproduct.

5. The method of claim 4, wherein the step of assigning includes a step of comparing a signal detected from each partition of the plurality with the threshold, and wherein the signal represents photoluminescence detected from the generic reporter.

6. The method of claim 4, wherein the threshold corresponds to a strength of the signal that is intermediate respective signal strengths for partitions exhibiting detectable amplification of the target and partitions exhibiting detectable amplification of the byproduct.

7. The method of claim 4, wherein partitions exhibiting detectable amplification of neither the target nor the byproduct have a signal strength that is less than the signal strength of partitions exhibiting detectable amplification of the byproduct.

8. The method of claim 4, further comprising a step of choosing the threshold based on respective signal strengths of partitions exhibiting detectable amplification of the target and partitions exhibiting detectable amplification of the byproduct.

9. The method of claim 4, wherein partitions exhibiting detectable amplification of the target have a stronger signal than partitions exhibiting detectable amplification of the byproduct.

10. The method of claim 4, wherein the step of determining a level of the target includes a step of calculating a concentration based on a number of the plurality of partitions that are assigned as positive for the target or based on a number of the plurality of partitions that are assigned as negative for the target.

11. The method of claim 1, wherein the target and byproduct amplicons have different lengths.

12. The method of claim 1 or claim 11, wherein the generic reporter binds to an amplicon in a quantity proportional to a length of the amplicon.

13. The method of claim 1 or claim 11, wherein the generic reporter binds to the amplicons nonspecifically.

14. The method of claim 1 or claim 11, wherein the generic reporter comprises a dye that binds to the amplicons nonspecifically.

15. The method of claim 1, wherein the determining step comprises classifying droplets positive only for the primer dimer as negative for the target.

\* \* \* \* \*